US012685715B2

(12) United States Patent
Chauhan et al.

(10) Patent No.: US 12,685,715 B2
(45) Date of Patent: *Jul. 21, 2026

(54) COMPOSITIONS, METHODS OF TREATMENT, AND CONTAINERS INCLUDING COMPOSITIONS

(71) Applicant: University of Florida Research Foundation, Inc., Gainesville, FL (US)

(72) Inventors: Anuj Chauhan, Gainesville, FL (US); Phillip J. Dixon, Gainesville, FL (US)

(73) Assignee: University of Florida Research Foundation, INC., Gainesville, FL (US)

( * ) Notice: Subject to any disclaimer, the term of this patent is extended or adjusted under 35 U.S.C. 154(b) by 392 days.

This patent is subject to a terminal disclaimer.

(21) Appl. No.: 18/237,920

(22) Filed: Aug. 25, 2023

(65) Prior Publication Data

US 2023/0404947 A1     Dec. 21, 2023

Related U.S. Application Data

(60) Continuation of application No. 17/824,235, filed on May 25, 2022, now Pat. No. 11,771,665, which is a division of application No. 16/418,061, filed on May 21, 2019, now Pat. No. 11,406,607.

(60) Provisional application No. 62/675,818, filed on May 24, 2018.

(51) Int. Cl.

| | |
|---|---|
| *A61K 31/145* | (2006.01) |
| *A45C 11/00* | (2006.01) |
| *A61F 9/00* | (2006.01) |
| *A61K 9/00* | (2006.01) |
| *A61K 47/22* | (2006.01) |
| *A61K 47/42* | (2017.01) |

(52) U.S. Cl.
CPC .......... *A61K 31/145* (2013.01); *A45C 11/005* (2013.01); *A61F 9/0008* (2013.01); *A61K 9/0048* (2013.01); *A61K 47/22* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 4,413,051 | A | 11/1983 | Thomas |
| 6,113,927 | A | 9/2000 | Hatakeyama |
| 6,558,762 | B2 | 5/2003 | Cahill et al. |
| 9,732,167 | B2 | 8/2017 | Okada et al. |
| 2005/0048122 | A1 | 3/2005 | Grabowski |
| 2009/0028841 | A1 | 1/2009 | Gohil |
| 2015/0174160 | A1 | 6/2015 | Pravda |
| 2015/0368022 | A1 | 12/2015 | Okada et al. |

| | | | |
|---|---|---|---|
| 2017/0088333 | A1 * | 3/2017 | Devouassoux .... A61B 50/3001 |
| 2020/0093764 | A1 | 3/2020 | Hershey et al. |
| 2021/0369649 | A1 | 12/2021 | Fedorchak et al. |

OTHER PUBLICATIONS

Hsu, K.-H., et al., Feasibility of corneal drug delivery of cysteamine using vitamin E modified silicone hydrogel contact lenses, European Journal of Pharmaceutics and Biopharmaceutics 85 (2013) 531-540 (Year: 2013).*

Biaglow, John E., et al. "Factors Influencing the Oxidation of Cysteamine and Other Thiols: Implications for Hyperthermic Sensitization and Radiation Protection." Radiation Research, 1984, pp. 298-312, vol. 100, No. 2, Radiation Research Society, https://www.jstor.org/stable/3576351.

Svensson, Björn E., "Abilities of Peroxidases to Catalyse Peroxidase-Oxidase Oxidation of Thiols." Biochemical Journal, 1988, pp. 757-762, vol. 256, Great Britain.

Iwata, Fumino, et al., "A Randomized Clinical Trial of Topical Cysteamine Disulfide (Cystamine) versus Free Thiol (Cysteamine) in the Treatment of Corneal Cystine Crystals in Cystinosis," Molecular Genetics and Metabolism, 1998, pp. 237-242, vol. 64, No. GM982725.

Labbé, Antoine, et al., "A New Gel Formulation of Topical Cysteamine for the Treatment of Corneal Cystine Crystals in Cystinosis: The Cystadrops OCT-1 Study," Molecular Genetics and Metabolism, Program and Abstracts for the 2014 Meeting of the Society for Inherited Metabolic Disorders, 2014, 111, pp. 314-320, vol. 111, doi: 10.1016/j.ymgme.2013.12.298.

Huynh, Nancy, et al., "Cysteamine Ophthalmic Solution 0.44% for the Treatment of Corneal Cystine Crystals in Cystinosis," Expert Review of Ophthalmology, 2013, p. 341+, vol. 8, No. 4, Expert Reviews Ltd., doi: 10.1586/17469899.2013.814885.

Lim, Lik Thai, et al., "Common Eye Drops and Their Implications for pH Measurements in the Management of Chemical Eye Injuries," International Journal of Ophthalmology, 2014, pp. 1067-1068, vol. 7, No. 6, doi: 10.3980/j.issn.2222-3959.2014.06.29.

Bozdag, Sibel, et al., "Formulation and in Vitro Evaluation of Cysteamine Hydrochloride Viscous Solutions for the Treatment of Corneal Cystinosis," European Journal of Pharmaceutics and Biopharmaceutics, 2008, pp. 260-269, vol. 70, doi: 10.1016/j.ejpb.2008.4.10.

Makuloluwa, K., et al., "Cysteamine hydrochloride eye drop solution for the treatment of corneal cystine crystal deposits in patients with cystinosis: An evidence-based review," Clinical Ophthalmology, 2018, pp. 227-236, vol. 12, doi: 10.2147/OPTH.S133516.

Quijano, Celia, et al., "Pathways of Peroxynitrite Oxidation of Thiol Groups," Biochemical Journal, 1997, pp. 167-173, vol. 322, Great Britain.

(Continued)

*Primary Examiner* — H. Sarah Park
(74) *Attorney, Agent, or Firm* — Thomas |Horstemeyer LLP.

(57) ABSTRACT

Compositions for treatment of cystinosis, products for administering eye drops, and products for storing contact lenses are provided. Compositions include solutions that can contain an effective amount of cysteamine to treat cystinosis, and an oil with a lower density than the solution. Also provided is a product including a bottle for containing a solution, the bottle being substantially free of $O_2$. Also provided is a contact lens holder for storing one or more contact lenses in a solution, the holder including barrier layers reducing the amount of $O_2$ entering the contact lens holder.

11 Claims, 5 Drawing Sheets

(56)          References Cited

OTHER PUBLICATIONS

Luo, Dayong, et al., "Kinetics and Mechanism of the Reaction of Cysteine and Hydrogen Peroxide in Aqueous Solution," Journal of Pharmaceutical Sciences, 2005, pp. 304-316, vol. 94, No. 2, doi: 10.1002/jps.20253.

Kachur, Alexander V., et al., "Mechanism of Copper-Catalyzed Oxidation of Glutathione," Free Radical Research, 1998, pp. 259-269, vol. 28, No. 3, doi: 10.3109/10715769809069278.

Christen, William G, et al., "Design of Physicians' Health Study II—A Randomized Trial of Beta-Carotene, Vitamins E and C, and Multivitamins, in Prevention of Cancer, Cardiovascular Disease, and Eye Disease, and Review of Results of Completed Trials," Annals of Epidemiology, 2000, pp. 125-134, vol. 10, No. 2.

Bursell, S E, et al., "High-Dose Vitamin E Supplementation Normalizes Retinal Blood Flow and Creatinine Clearance in Patients with Type 1 Diabetes," Diabetes Care, 1999, pp. 1245-1251, vol. 22, No. 8.

Padayatty, Sebastian J., et al., "Vitamin C as an Antioxidant: Evaluation of Its Role in Disease Prevention," Journal of the American College of Nutrition, 2003, pp. 18-35, vol. 22, No. 1, American College of Nutrition.

Christen, William G., et al., "Antioxidants and Age-Related Eye Disease Current and Future Perspectives," Annals of Epidemiology, 1996, pp. 60-66, vol. 6, No. 1.

Coupland, John N., and D. Julian McClements, "Lipid Oxidation in Food Emulsions," Trends in Food Science & Technology, 1996, pp. 83-91, vol. 7.

Hsu, Kuan-Hui, et al., "Feasibility of Corneal Drug Delivery of Cysteamine Using Vitamin E Modified Silicone Hydrogel Contact Lenses," European Journal of Pharmaceutics and Biopharmaceutics, 2013, pp. 531-540, vol. 85, doi: 10.1016/j.ejpb.2013.4.017.

Phillip, Dixon, et al., "In vitro drug release and in vivo safety of vitamin E and cysteamine loaded contact lenses," International Journal of Pharmaceutics, 2018, pp. 380-391, vol. 544, doi: 10.1016/j.ijpharm.2017.11.059.

Sapei, Lanny, and Lie Hwa, "Study on the Kinetics of Vitamin C Degradation in Fresh Strawberry Juices," Procedia Chemistry, International Conference and Workshop on Chemical Engineering UNPAR 2013 (Icce Unpar 2013), 2014, pp. 62-68, vol. 9, doi: 10.1016/j.proche.2014.5.008.

Chan, Alvin C., "Partners in Defense, Vitamin E and Vitamin C," Canadian Journal of Physiology and Pharmacology, 1993, pp. 725-731, vol. 71, Canada.

Poljsak, Borut and Peter Raspor, "The antioxidant and pro-oxidant activity of vitamin C and trolox in vitro: a comparative study," Journal of Applied Toxicology, 2008, pp. 183-188, vol. 28, doi: 10.1002/jat. 1264.

Zeida, Ari, et al., "Molecular Basis of the Mechanism of Thiol Oxidation by Hydrogen Peroxide in Aqueous Solution: Challenging the SN2 Paradigm," Chemical Research in Toxicology, 2012, pp. 741-746, vol. 25, ACS Publications, doi: 10.1021/tx200540z.

De Rycker, Johan and Barry Halliwell, "Oxidation of Thiol Compounds by Catalase and Peroxidase in the Presence of Manganese (II) and Phenols," Biochemical Society Transactions, 1978, pp. 1343-1345, vol. 6, doi: 10.1042/bst0061343.

Chaix, Estelle, et al., "Oxygen and Carbon Dioxide Solubility and Diffusivity in Solid Food Matrices: A Review of Past and Current Knowledge," Comprehensive Reviews in Food Science and Food Safety, 2014, pp. 261-286, vol. 13, doi: 10.1111/1541-4337.12058.

"Innovative Plastics Oxygen and Water Permeability", SABIC, pp. 1-3, (2013).

* cited by examiner

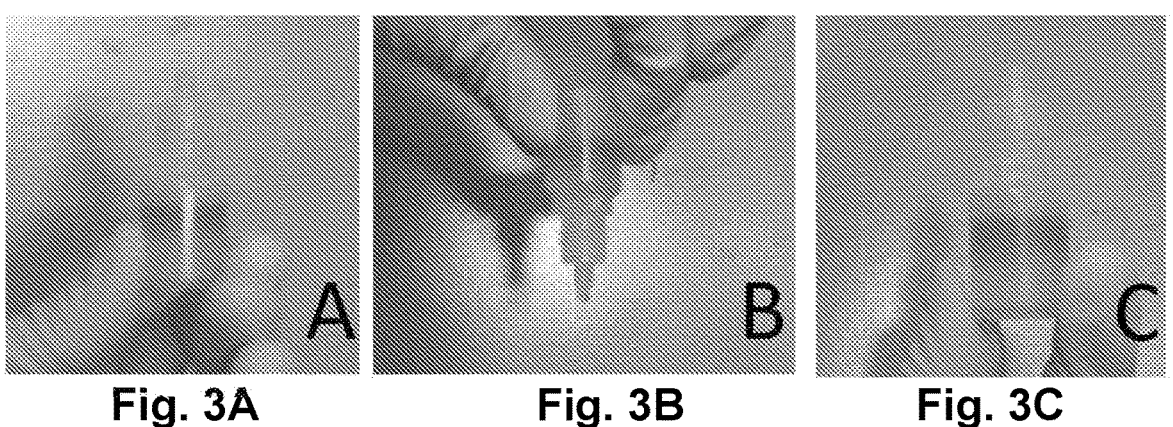
Fig. 3A　　　　　Fig. 3B　　　　　Fig. 3C
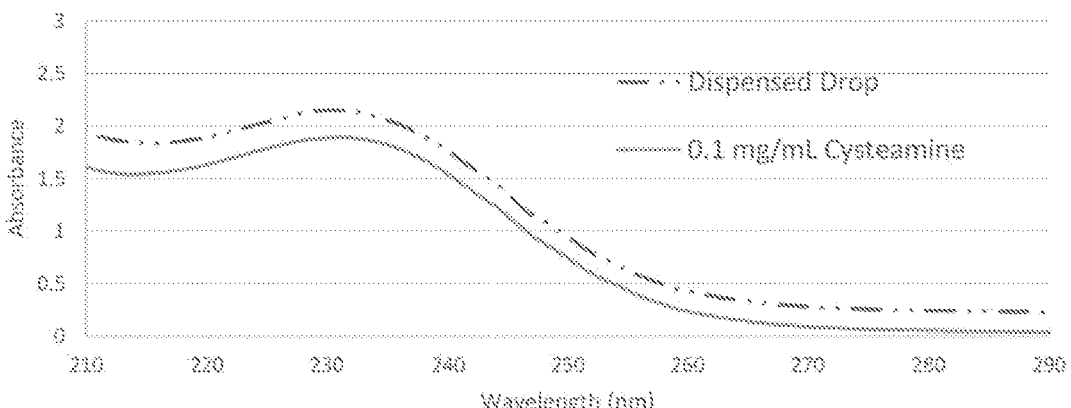
Fig. 3D
Fig. 4

COMPOSITIONS, METHODS OF TREATMENT, AND CONTAINERS INCLUDING COMPOSITIONS

CROSS-REFERENCE TO RELATED APPLICATIONS

This application is a continuation of U.S. Non-Provisional application Ser. No. 17/824,235, having the title "COMPOSITIONS, METHODS OF TREATMENT, AND CONTAINERS INCLUDING COMPOSITIONS", filed on May 25, 2022, which is a divisional of U.S. Non-Provisional application Ser. No. 16/418,061, having the title "COMPOSITIONS, METHODS OF TREATMENT, AND CONTAINERS INCLUDING COMPOSITIONS", filed on May 21, 2019, which application claims priority to U.S. Provisional Application Ser. No. 62/675,818, having the title "COMPOSITIONS, METHODS OF TREATMENT, AND CONTAINERS INCLUDING COMPOSITIONS", filed on May 24, 2018, which are entirely incorporated herein by reference.

BACKGROUND

Cystinosis is a genetic disorder affecting transport of the amino acid cysteine across the lysosomal membrane, which causes crystal formation in many organs including kidneys and cornea. If left untreated, cystinosis can lead to renal failure, stunted growth, and blindness. The disease in managed by a hydrophilic drug cysteamine that reacts with cysteine through a thiol-disulfide interchange to form cysteine-cysteamine dimers that can then be transported out of the cell [6,7]. The drug is administered orally as well as topically via eye drops because the systemic drug does not reach the cornea at sufficient concentration. The approved US formulation (CYSTARAN™) is a 0.44% cysteamine solution that must be administered hourly. A 0.38% gel formulation (Cystadrops®) is recently approved for marketing in Europe. While CYSTARAN™ and Cystadrops® are effective at treating cystinosis, they both suffer from a short shelf life upon opening because of cysteamine oxidation from exposure to air. The thiol group in cysteamine readily reacts with oxygen to form a disulfide called cystamine, which is ineffective at treating the cysteine crystals in the cornea. CYSTARAN™ is packaged in LDPE bottles which is permeable to oxygen and so the eye drop bottles are shipped frozen to minimize the oxidation allowing extended shelf life of a year. The formulation is thawed prior to use by the patient. CYSTARAN™ is formulated at a pH of between 4.1 and 4.5, possibly to increase the stability. These approaches keep the formulation stable during shelf life, but the oxidation starts after the formulations are thawed, which limits the maximum duration of use after opening to about a week. The costs of CYSTARAN™ increase due to the complicated shipping under frozen conditions by around $8,000 per year. Thus, designing a formulation that does not require the drug to be frozen could lower this cost. The lower pH of CYSTARAN™ could have potential for side effects such as a burning sensation upon application and so it could be further useful to design a stable formulation at the pH of around 7.

Cystadrops® are stored in a sealed amber vial with a bromobutyl stopper and aluminum seal, which have a dramatically lower oxygen permeability compared to LDPE allowing extended shelf life at room temperature. When the formulation is ready to use, the seal and stopper are removed and replaced with a PVC and HDPE dropper. Cystadrops® is a gel formulation, which uses carmellose sodium to enhance the tear residence time. Other gel formulations have also been explored for increased stability such as a formulation with hydroxypropylmethylcellulose (H PMC) which was stable for a year when stored in a sealed glass flagon. However, similar to CYSTARAN™, Cystadrops® have a recommended shelf life of one week after opening due to oxygen entering the system through the dropper. While the amber vial does increase shelf life before opening, it does not increase the shelf life after opening as compared to CYSTARAN™, likely because there is no mechanism to protect the formulation from the air that enters the bottle when the drops are administered.

Therefore, new methods for limiting oxygen exposure to the formulation are needed to increase the shelf life and lower the cost of the treatment.

SUMMARY

Embodiments of the present disclosure provide for compositions for treatment of cystinosis, products for administering eye drops, products for storing contact lenses, and the like.

An embodiment of the present disclosure includes compositions including solution that can contain an effective amount of cysteamine or derivatives thereof to treat cystinosis, and an oil that can have a lower density than the solution.

An embodiment of the present disclosure also includes a product including a bottle containing a solution. Within the bottle, the environment not occupied by the solution can be substantially free of $O_2$. The solution can include an effective amount of cysteamine or derivatives thereof to treat cystinosis, and an oil having a lower density than the solution.

An embodiment of the present disclosure also includes a product including a contact lens holder for storing one or more contact lenses in a solution. The solution and the lens can include an effective amount of cysteamine or derivatives thereof to treat cystinosis. The contact lens holder can include at least one barrier layer, wherein each of the barrier layers reduces the amount of $O_2$ entering the contact lens holder as compared to a contact lens holder without the barrier layer.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1A-10 show degradation of (FIG. 1A) 0.01% cysteamine in anti-oxidant formulations; (FIG. 10) 0.44% cysteamine in eye drop bottles with different packaging. All experiments were conducted at pH=7 and room temperature (25° C.).

(FIG. 2A) LDPE (left) and OMAC®-covered (right); (FIG. 2B) Heat-sealed storage pouches for eye drop bottles and contact lenses for storage trial: OMAC® (left) and foil (right).

FIGS. 3A-3C show drop dispensing from a formulation containing 1 cm thick oil layer on top of the formulation to reduce exposure to oxygen. (FIG. 3A) Before inverting bottle; (FIG. 3B) Inverting bottle and dispensing drop; (FIG. 3C) Returning bottle to original position results in gradual return of separated hydrophobic layer. FIG. 3D provides a comparison of spectra between dispensed drop and cysteamine.

FIG. 4 includes a pair of eye dropper bottles, where it is shown how $O_2$ enters a traditional eye dropper bottle and how $O_2$ entering is limited using an eye dropper bottle of the present disclosure.

FIG. 5 illustrates a bottle in accordance with embodiments of the present disclosure.

FIG. 6 illustrates a bottle in accordance with embodiments of the present disclosure.

Figure 1A:
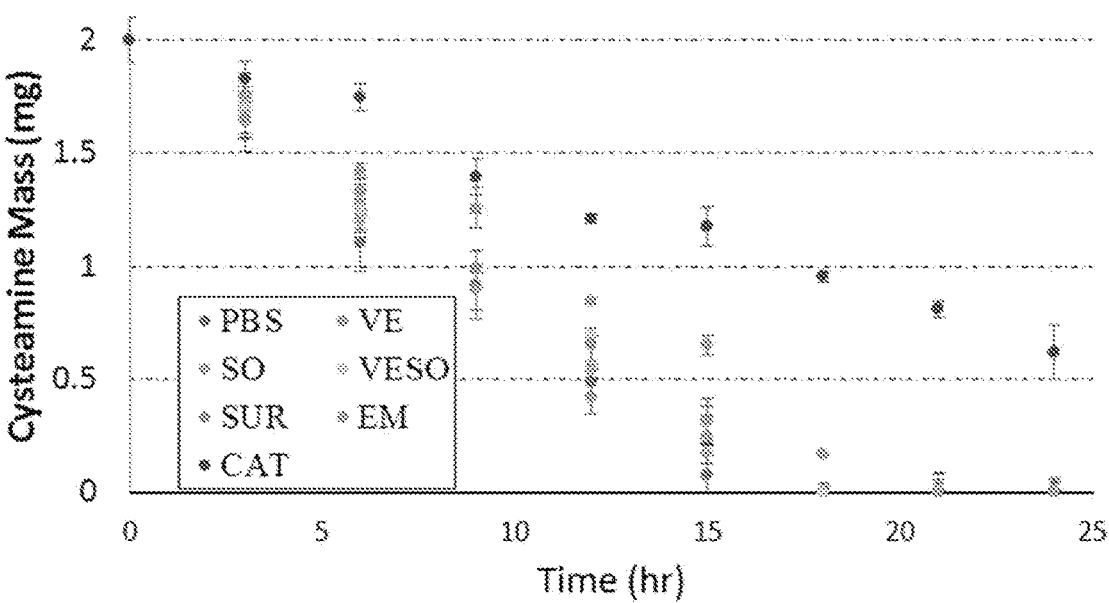

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, and the like, which are within the skill of the art.

The following examples are put forth so as to provide those of ordinary skill in the art with a complete disclosure and description of how to perform the methods and use the compositions, methods, and containers disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Definitions

By "administration" is meant introducing composition (e.g., the composition or ophthalmic composition) of the present disclosure into a subject. The route of administration can include topical (e.g., via the eye using an eye drop).

The terms "therapeutically effective amount" and "an effective amount" are used interchangeably herein and refer to that amount of the composition (e.g., the composition or ophthalmic composition) being administered that is sufficient to affect the intended result. For example, an effective amount of the can be used to treat a disease like cystinosis. The therapeutically effective amount may vary depending upon the intended application (in vitro or in vivo), or the subject, e.g., the weight and age of the subject, the manner of administration and the like, which can readily be determined by one of ordinary skill in the art. The specific dose will vary depending on the particular agent chosen, the dosing regimen to be followed, whether it is administered in combination with other agents, timing of administration, and the physical delivery system in which it is carried.

The term "unit dosage form," as used herein, refers to physically discrete units suitable as unitary dosages for human and/or animal subjects, each unit containing a predetermined quantity of the composition calculated in an amount sufficient to produce the desired effect in association with a pharmaceutically acceptable diluent, carrier or vehicle. The specifications for unit dosage forms depend on the particular composition employed, the route and frequency of administration, and the effect to be achieved, and the pharmacodynamics associated with composition in the subject.

As used herein, a "pharmaceutical composition" and a "pharmaceutical formulation" are meant to encompass embodiments of the present disclosure (e.g., the composition or ophthalmic composition) suitable for administration to a subject, such as a mammal, especially a human. In general, a "pharmaceutical composition" or "pharmaceutical formulation" is sterile, and preferably free of contaminants that are capable of eliciting an undesirable response within the subject (e.g., the composition).

As used herein, the terms "treatment", "treating", and "treat" are defined as to achieve a desired result (e.g., treat cystinosis) using the composition (e.g., the composition or ophthalmic composition). "Treatment", as used herein, covers any treatment in a subject (e.g., a mammal, typically a human or non-human animal of veterinary interest).

As used herein, the term "subject" or "patient" includes humans, mammals (e.g., cats, dogs, horses, etc.), birds, and the like. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a subject. The term "living subject" refers to the entire subject or organism and not just a part excised (e.g., a liver or other organ) from the living subject.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition (e.g., composition or ophthalmic compositions) or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds (e.g., composition or ophthalmic compositions) of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenyl propionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds (e.g., composition or ophthalmic compositions) of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition of the present disclosure are also contemplated herein.

To the extent that the disclosed the compounds (e.g., composition or ophthalmic compositions) of the present disclosure, and salts thereof, may exist in their tautomeric form, all such tautomeric forms are contemplated herein as part of the present disclosure.

All stereoisomers of the compounds of the (e.g., composition or ophthalmic compositions) of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds (e.g., composition or ophthalmic compositions) of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3): 183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm.

Sci., 11 Suppl 2:S15-27; Wang, W. et al. (1999) Prodrug approaches to the improved delivery of peptide drugs. Curr. Pharm. Des., 5(4):265-87.

General Discussion

Aspects of the present disclosure provide for compositions, ophthalmic compositions (e.g., pharmaceutical composition), methods of use, bottles for the compositions and the ophthalmic compositions, containers for the compositions and the ophthalmic compositions, and the like. Presently, eye drops including cysteamine require special handling due to the oxidization of cysteamine. For example, the eye drops are frozen during processing and handling to the pharmacy and then are also frozen by the patient until used. Once thawed, the cysteamine oxidizes within about a week. The shelf life and use life of eye drops including cysteamine is very short and increases the costs associated purchasing these eye drops as well as affects the efficacy of the eye drops. An advantage of embodiments of the present disclosure includes reducing the rate at which the cysteamine oxidizes so that the shelf life and/or the use life (e.g., over two weeks) are extended.

In an aspect, the composition or ophthalmic composition (reference to "composition" includes reference to both the "composition" and the "ophthalmic composition" and is done for ease of reading) includes a solution including an effective amount of cysteamine or derivatives thereof and an oil, where the oil has a lower density than the solution so that the oil forms an oil layer on top of the solution. While in a container (e.g., eye drop bottle), the oil reduces the rate at which the oxygen present in the environment above the composition diffuses into the solution.

In an aspect, the solution (e.g., aqueous solution) can include cysteamine, derivatives thereof, and salts thereof as well as optionally an isotonic agent, a buffering agent, a stabilizer, a pH adjusting agent and the like. In an aspect, the solution includes about 2 to 10 mg/15 ml of cysteamine, depending upon the form of cysteamine. In an aspect, the amount of cysteamine can be about 4.4 mg/15 ml of cysteamine, and when cysteamine is in the form of cysteamine hydrochloride it can be about 6.5 mg/15 ml.

Examples of cysteamine derivatives include: 2-methylthio ethylamine (cinnamate), 2-methyl thio ethylurea, N-(2-methylthio ethyl)p-acetamido benzamide, 2-aminoethanethiol, N-(2-methylthio ethyl)p-acetamido benzenesulfonamide, N-(2-propylthioethyl)-p-methoxy benzamide, N-(butylthio ethyl) nicotinamide, N-(2-dodecylthio ethyl)p-butoxybenzamide, N-(2-methylthio ethyl)p-toluenesulfonamide, N-(2-isopropylthio ethyl)propionamide, N-(2-octylthio ethyl)acetamide, N-(2-butylthio ethyl) methanesulfonamide, N-(2-isopentylthio ethyl)butane, bis 1,4-(2-acetamido ethylthio), 2,3-butanediol, 2-hexadecylthio ethylamine hydrochloride, 2-allylthio ethylamine malate, 9-octadecene 2-ylthio ethylamine hydrochloride, 2-dodecylthio ethylamine hydrochloride, 2-isopentylthio ethylamine mandelate, 2-octadecylthio ethylamine salicylate, 28-hydroxyethyl thio ethylurea, 2-β-hydroxy ethylthio ethylamine hydrochloride, 2-(2,3-dihydroxy propylthio)ethylamine p-toluenesulfonate, 2-(2-hydroxy propylthio)ethylamine oxalate, N-(2-methylthio ethyl)phenylacetamide, 2-(2,2-dimethoxy ethylthio)ethylamine hydrochloride, 2-(2,2-dimethoxy ethylthio)ethylamine undecylenate, 2-(2,2-diethoxy ethylthio)ethylamine undecylenate, 2-(2,2-diethoxy ethylthio)ethylamine acetate, 2-undecenylthio ethylamine, 2-β-ureidoethylthio ethylamine hydrochloride, 2-β-acetamidoethylthio ethylamine tropate, 2,2'-thio diethylamine fumarate, 2,2'-thio diethylurea, 3-β-aminoethylthio propylamine hydrochloride, S β-ureidoethyl thiocarbamate, 2-ethoxycarbonylthio ethylamine hydrochloride, 2-dimethylamino carbonylthio ethylamine sulfate, 2-butoxycarbonyl methylthio ethylurea, 2-ethyloxycarbonylmethylthio ethylamine hydrochloride, 6-β-aminoethylthio hexanoate of methyl hydrochloride, 5-β-aminoethylthio pentanoic acid, 2-phenylthio ethylamine dihydrogen phosphate, 2-p-t-butylphenylthio ethylamine trichloracetate, 2-p-methoxyphenylthio ethylamine ditartrate, 2-tolylthio ethylamine hydrobromide, 2-(1-biphenyl thio)ethylamine hydrochloride, 2-N-pentachlorophenylthio ethyl acetamide, 2-benzylthio ethylamine malate, 2-benzylthio ethylamine nicotinate, 2-benzylthio 2-methyl propylamine hydrochloride, 2-benzylthio propylamine lactate, N-(2-benzylthio ethyl)nicotinamide hydrochloride, N-(2-benzylthio ethyl)10-undecene amide, N-(2-benzylthio ethyl)hexadecanamide, S-8-aminoethyl mercaptobutyric acid, N-(2-benzylthio ethyl)formamide, N-(2-benzylthio ethyl)phenylacetamide, N-[2-(2,6-dimethyl phenyl)ethyl]hexanamide, 2-o-aminophenylthio ethylamine succinate, N-(2-benzylthio ethyl)glutamine, S-8-aminoethyl mercapto acetic acid (3-S-8-aminoethyl)mercapto propionic acid, (3-S-.gamma.-amino propyl)mercapto acetic acid, S(2-p-methoxybenzamido ethyl)mercapto 2-(2-naphtyl methylthio)ethylamine hydrochloride, 2-(2-naphtyl methylthio)ethylamine disuccinate, (2-thenyl)2-thio ethylamine hydrobromide, 2-N-acetyl(2-thenylthio-ethylamine, 2-o-chlorobenzylthio ethylamine hydrochloride, 2-p-chlorobenzylthio ethylamine glycolate, 2-o-fluorobenzylthio ethylamine hydrochloride, 2-furfurylthio ethylamine hydrochloride, 2-tetrahydrofurfurylthio ethylamine p-amino-benzoate, 2-β-phenylethylthio ethylamine glutamate, 2-diphenylmethylthio ethylamine hydrochloride, 2-triphenyl methylthio ethylamine hydrochloride hemihydrate, 2-(2-pyridyl ethylthio)ethylamine hydrochloride, 2-(2-p-toluene sulfonamido ethylthio)pyridine N-oxide, 2-β-aminoethylthiomethyl pyridine N-oxide dihydrochloride, 2-β-aminoethylthio pyridine N-oxide hydrochloride, 2,4-dichloro 2-benzylthio ethylamine aspartate, N-[2-(3,4-dichloro benzylthio) ethyl]butyramide, N-[2-(2,6-dichloro benzylthio)ethyl] dodecanamide, N-[2-(3,5-dichloro benzylthio)ethyl] trifluoroacetamide hydrochloride, 2-p-ethoxybenzylthio ethylamine hydrochloride, N-[2-m-fluorobenzylthio ethyl] chloroacetamide, 2-p-bromobenzylthio ethylamine succinate, 2-(3,4-dimethoxy benzylthio)ethylamine malate, 2-(3, 4-methylenedioxy benzylthio)ethylamine hydrochloride, 2-(2,4-dichloro cetylthio)ethylamine, 2 (3,4,5-trimethoxy benzylthio)ethylamine hydrocinnamate, 2-p-methoxy benzylthio ethylamine salicylate, 2-o-methylbenzylthio ethylamine phenylacetate, N-[2-p-dimethylaminobenzylthio ethyl]methane-sulfonamide, 2-p-phenoxybenzylthio ethylamine hydrochloride, 2-β-aminoethylthio pyridine hydrochloride, 2-benzylthio ethylamine citrate, N-[2-benzylthio ethyl]2,4-dihydroxy 3,3-dimethyl butyramide, N-(2-benzylthio ethyl) 6,8-dihydroxy 7,7-dimethyl 5-oxo 4-aza octanamide, N-[2-(2-pyridyl thio)ethyl]propionamide, 2-(2-pyridyl methylthio)ethylamine dihydrochloride, 2-benzylthio ethyl amine pantothenate, S-(β-acetamidoethyl)mercapto acetate of β-morpholinoethyl, S-(8-phenylacetamidoethyl)mercaptoacetate N'-methyl 2-piperazino ethyl, S-(β-ureidoethyl)mercaptoacetate of β-pyrrolidinoethy, S-(β-trifluoroacetamidoethyl)-.beta.mercapto-propionate of β-dimethyl amino ethyl, 2-p-nitrobenzylthio ethylamine crotonate, 2-β-morpholinocarbonyl ethylthio ethylamine hydrochloride, N,N-di(hydroxyethyl)S-(β-benzamido-ethyl)mercapto-acetamido, N[2-N'-methyl piperazino carbonylthio ethyl]acetamide, 2-(1-naphthyl thio)ethylamine hydrochloride, N-(3-β-ureidoethylthio propyl) succinamic acid, 3-allylthio propylamine, 3-(2,2'-dimethoxy ethylthio)propylamine, 3-(2,2'-dimethoxy ethylthio)propylamine sulfate, S-β-aminoethylmercapto acetic acid, the hydrochloride of S-.beta.-aminoethyl mercapto acetic acid, N-(2-benzylthioethyl)acetamide, N-(2-benzylthioethyl)propionamide, N-(2-benzylthioethyl)butyramide, N-(2-benzylthioethyl)methanesulfonamide, N-(2-benzylthioethyl)ethanesulfonamide, N-(2-benzylthioethyl-propanesulfonamide, N-(2-benzylthioethyl)butanesulfonamide, S-(2-p-acetamidobenzenesulfonamido ethyl)mercapto acetic acid, S-(2-p-acetamidobenzamido ethyl)mercapto acetic acid, N-(2-thenylthioethyl)acetamide, 2-benzylthio propylamine, 2-benzylthio 2-methyl propylamine, 2-(2-p-toluenesulfonamido ethylthio)pyridine N-oxide, S-(2-p-butoxybenzamidoethyl) mercapto acetic acid, 2-t-butylthio ethylamine hydrochloride, 2-methoxy carbonyl methylthio ethylamine hydrochloride, 2-ethoxycarbonylmethylthio ethylamine hydrochloride, 2-propoxycarbonylmethyl thio ethylamine hydrochloride, 2-butoxycarbonylmethylthio ethylamine hydrochloride, 2,2'-thio diethylamine dihydrochloride, 3-(2-aminoethylthio)alanine hydrochloride, 2-benzylthio ethylammonium diacid phosphate, 2-methylthio ethylamine, N-(methylthioethyl)p-acetamidobenzamide, N-(2-methylthioethyl) nicotinamide, N-(2-methylthioethyl)benzamide, N-(2-methylthioethyl)p-butoxybenzamide, N-(2-methylthioethyl)butyramide, N-(2-methylthioethyl)propionamide, N-(2-methylthioethyl)acetamide, N-(2-methylthioethyl)butanesulfonamide, N-(2-octylthioethyl)methanesulfonamide, 2-cetylthio ethylamine hydrochloride, 2-(2-hydroxyethylthio)ethylamine hydrochloride, 2-methylthio ethylamine phenylacetate and 2-methylthio ethylamine undecylenate.

In an aspect, the oil can include oils that can be used in ophthalmic solutions, where the oil is substantially immiscible in the solution. While all oils are at least partially miscible in solution, oils used herein form two layers, where the oil forms the oil layer on top of the solution. The thickness of the oil layer can be about 0.5 mm to 2 cm or about 1 mm to 1 cm. In an aspect, the oil can be an antioxidant oil such as Vitamin E including both tocopherols and tocotrienols, natural antioxidant such as glutathione and a combination thereof. In an aspect, the oil can be essential or vegetable oils (i.e. soybean oil, olive oil, sesame oil, cotton seed oil, castor oil, sweet almond oil), mineral oil (i.e. petrolatum and liquid paraffin), medium chain triglycerides (MCT) (i.e. a triglyceride oil in which the carbohydrate chain has about 8-12 carbon atoms), oily fatty acid, isopropyl myristate, oily fatty alcohols, esters of sorbitol and fatty acids, oily sucrose esters, silicon oil, and in general any oily substance which is physiologically tolerated. In an aspect, the oil can be about 0.001 to 30% or about 0.01 to 5% of the composition. The oil layer on the top of the formulation can be about 0.1 to 20 mm or 1 to 10 mm.

In an aspect, the solution can also include catalase. Catalase can slow down the oxidation by reacting with the oxygen ions once the $O_2$ diffuses through the oil layer and into the solution. In an embodiment, the amount of catalase in the solution can be about 0.5 to 3% or about 0.15% of the solution.

In an aspect, the solution can contain other natural compounds that are well known antioxidants such as haldi extract, green tea extract, essential oils. In an aspect, the solution can contain nutraceuticals such as curcumin extract, green tea extract, essential oils (e.g., oils from plants), Vitamin E that serve the dual purpose of anti-oxidants to prevent oxidation of the drug, and also protect ocular tissue after instillation. In an aspect, the hydrophobic antioxidants and/or nutraceuticals are dispersed by using emulsifiers to form emulsions. In an aspect, the natural components added to the formulation can act as preservatives eliminating the need of benzalkonium chloride, which causes damage of the ocular epithelia. For example, garlic and curcumin/haldi extract are known for antibiotic properties. In an aspect, the natural components can be used in combination with benzalkonium chloride or other preservatives.

As briefly described above, the composition can further comprise pharmaceutically acceptable additives. The pharmaceutically acceptable additive can be a carrier or diluent that does not remarkably stimulate an organism and hinder biological activity and properties of an administrated active ingredient. An example of the pharmaceutically acceptable additive is an isotonic agent, a buffering agent, a stabilizer, a pH adjusting agent and the like.

In an aspect, the composition is desirably a liquid medicine, so may further comprise a carrier including an aqueous solution. In aspects, the carrier including an aqueous solution may include one or more pharmaceutically acceptable carriers such as distilled water, phosphate buffered saline, a balanced salt solution, and saline. The content of the used carrier may be adjusted according to the amount required for the total capacity of an eye drop to be prepared.

In an aspect, the composition can also comprise a pharmaceutically acceptable salt. An example of the pharmaceutically acceptable salt may be hydrochloric acid, sodium chloride, potassium chloride, and a mixture thereof.

In an aspect where the composition is used as an eye drop, the eye drop is a pulse entry of the drug (e.g., cysteamine), but the drug is rapidly diluted by tears and flushed out of the eye. Polymers are frequently added to ophthalmic solutions in order to increase the viscosity of the vehicle; this prolongs contact with the cornea, often enhancing bioavailability. The types of polymers permitted by the Federal Food and Drug Administration in ophthalmic solutions are defined concentrations of cellulose derivatives (methylcellulose, hydroxyethylcellulose, hydroxypropylcellulose and carboxymethylcellulose), dextran 70, gelatin, polyols, glycerin, polyethylene glycol 300, polyethylene glycol 400, polysorbate 80, propylene glyclol, polyvinyl alcohol and povidone, all of which (singly or in combination) are contemplated for use in the present disclosure.

In an aspect, the disclosed compositions (e.g., composition and ophthalmic composition) can comprise a neutralizing agent such as sodium hydroxide and organic bases in an amount of about 0 to about 2.5% by weight of the composition.

In an aspect, the composition (e.g., composition and ophthalmic composition) may include a demulcent such as carboxymethylcellulose sodium, hydroxypropyl methylcellulose, hydroxyethyl cellulose, methylcellulose, polyvinyl alcohol, povidone, glycerin, propylene glycol, PEG 300, PEG 400, and a combination thereof. The demulcent can be present in an amount of about 0 to about 10%, or about 2%, 5%, 7%, or 9%, by weight of the composition.

In an aspect, the composition comprises a tonicity agent such as sodium chloride, glycerin, mannitol, potassium chloride, erythritol, and a combination thereof, in an amount of about 0 to about 4% or about 0.01% to about 3% by weight of the composition.

In an aspect, the composition may include one or more buffering agents. Suitable buffering agents include, but are not limited to, phosphates, citrates, acetates, borates, and combinations thereof. The amount of buffer component employed is sufficient to maintain the pH of the composition in a range of about 6 to about 8, or from about 6.5 to about 7.5. In certain embodiments, the buffer is present in an amount of about 0 to about 2.0% by weight of the composition.

In an aspect, the composition includes a thickener or viscosity agent. The viscosity agent can be selected from the group consisting of carbomer, sodium carboxymethyl cellulose, methyl cellulose, hydroxypropyl methyl cellulose, polyvinyl alcohol, zanthan gum, and a combination thereof. The viscosity agent can be present in an amount of about 0% to about 4% or about 0.01% to about 3.0% by weight of the composition.

In an aspect, the composition includes a solubilizer or solubility enhancing agent. The solubilizer or solubility enhancing agent can be selected from the group consisting of cyclodextin, alpha-cyclodextrin, beta-cyclodextrin, gamma-cyclodextrin, hydroxypropyl-beta-cyclodextrin, sulfobutyl ether-p-cyclodextrin (Captisol®) and a combination thereof. The solubilizer or solubility enhancing agent can be present in an amount of about 0% to about 10%. In some embodiments, the solubilizer or solubility enhancing agent can be present in an amount of about 0.01% to about 7.0%. In some embodiments, the solubilizer or solubility enhancing agent can be present in an amount of about 0.1 to about 4% by weight of the composition.

In an aspect, the composition can include preservatives. Examples of preservatives are quaternary ammonium salts, such as cetrimide, benzalkonium chloride or benzoxonium chloride, alkyl-mercury salts of thiosalicylic acid, such as, for example, thimerosal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, or sorbic acid. Preferred preservatives are cetrimide, benzalkonium chloride, benzoxonium chloride and parabens. Where appropriate, a sufficient amount of preservative is added to the ophthalmic composition to ensure protection against secondary contaminations during use caused by bacteria and fungi.

According to one embodiment, the pH of the composition (e.g., composition and ophthalmic composition) should be as close to that of the tear film as possible. The physiologic pH of tears is approximately $7.4\pm0.2$. Thus, from a comfort, tolerability and safety perspective, this would be the optimal pH of ophthalmic preparations.

Stimulation of tear secretion and eye blinking causes the pH to decrease in value. When the eyelid remains open for extended periods of time the tear-film is alkalized by equilibrium with the partial pressure of $CO_2$ in the surrounding air and a pH value of greater than 9 is attained. Both decreases and increases in pH occur without adverse consequences. Thus, there is some latitude in the pH range when formulating inventive formulations around pH of approximately 7.4.

Also, when the composition is administered to the eye, it stimulates the flow of tears. Tear fluid is capable of quickly diluting and buffering small volumes of added substances, suggesting the eye can tolerate a fairly wide pH range offered by certain formulations.

Consequently, ophthalmic formulations may be within a range of from about pH 3.5 to 11.5. However, ophthalmic formulations may display pH ranges somewhat more narrowly from 3.5 to 9, preferably from 4.5 to 8 and most preferably from pH 5.5 to 7.8. The most preferred pH range is advantageous from the perspective solubility, chemical stability and therapeutic activity of the inventive composi-
tions and a useful and relatively narrow range to prevent
corneal damage.

In an aspect of the present disclosure, the method includes
treating cystinosis by topically administering an effective
amount of the composition or the ophthalmic composition to
an eye of the subject. In an aspect, the composition or the
ophthalmic composition can be administered uses a bottle
(e.g., eye dropper bottle). In an aspect, the frequency,
duration, and dosage of the administration are determined by
the prescribing physician, which are at least part determined
by age, weight, severity of disease, and the like. The dosage
can vary depending on the unit dosage form. When the
composition is a solution and is used an eye drop, for
example, 1, 2, 3, or more drops can be administered per eye
per administration. Frequency of administration can be one
or more times daily (such as once, twice, three, or four or
more times daily), bi-weekly, and/or monthly. Duration of
administration can continue until the condition to be treated
is resolved, that is, until one or more symptoms of the ocular
condition are reduced or eliminated. Accordingly, the com-
position can be administered for hours, days, weeks, months,
and years.

In an aspect of the present disclosure, a product can
include a bottle containing the composition as describe
herein, where the environment within (e.g., head space
above the oil layer) the bottle is substantially free of $O_2$. In
an embodiment, the environment can be made up of a gas or
gas mixture that does not or substantially (e.g., about 90%
or more, about 95% or more, about 99% or more, about
99.9% or more) does not include $O_2$. In an aspect, the gas
can include $N_2$ or an inert gas such as argon. In an aspect,
the bottle can include a tip (e.g., eye dropper tip) as part of
the bottle or as a separate part of the bottle (e.g., attached
using threads or the like), where the tip can be used to
control the drop size. In an aspect, the bottle can be made of
materials approved for eye drops. In an aspect, the tip can be
designed to scavenge oxygen entering the bottle, for
example, by packing a chemical such as iron oxide particles
that react with the oxygen.

In an aspect, the bottle includes at least one oxygen barrier
(e.g., 1 to 10 barrier layers). In an aspect, each barrier layer
is the same or one or more of the barrier layers can be of a
different type. In an aspect, the barrier layer reduces the
amount of oxygen from entering the bottle as compared to
a bottle without the barrier layer. In aspects, the barrier layer
can include three components such as a layer of ethylene
vinyl alcohol (EVOH), aluminum foil, and an iron based
absorbent layer, which can be purchase from Mitsubishi Gas
Chemical America under the Tradename OMAC® oxygen-
resistant material.

In an aspect, if the additive layers increase the rigidity of
the bottle to make drop dispensing require excessive force,
the material of the original, uncoated bottle can be chosen to
be thinner or more flexible/lower modulus. This will allow
patients to dispense the drops without the need for hard
squeeze. In an aspect, the bottle can have small regions of
low modulus where the patient is expected to squeeze to
instill the drops without the need for a hard squeeze.
Volumes and shapes of the bottle can be envisioned by one
of skill in the art. A typical eye drop bottle has a volume of
about 3-15 mL. During drop instillation, the bottle is
squeezed to decrease the volume. Since liquid is incom-
pressible, the gas phase in the bottle is reduced in volume
leading to a higher pressure that results in dispensing of the
eye drop.

In an aspect, the product can include the bottle disposed
into a container (e.g., a pouch) until use by the patient,
doctor, or nurse. In an aspect of the present disclosure, a
container can include an environment (e.g., space not occu-
pied by the bottle) that is substantially free of $O_2$. In an
embodiment, the environment can be made up of a gas or gas
mixture that does not or substantially (e.g., about 90% or
more, about 95% or more, about 99% or more, about 99.9%
or more) does not include $O_2$. In an aspect, the gas can
include $N_2$ or an inert gas such as argon. In an aspect, the
barrier layer reduces the amount of oxygen from entering the
container as compared to a container without the barrier
layer. In aspects, the barrier layer can include three compo-
nents such as a layer of ethylene vinyl alcohol (EVOH),
aluminum foil, and an iron based absorbent layer, which can
be purchased from Mitsubishi Gas Chemical America under
the Tradename OMAC® oxygen-resistant material. In as
aspect, the formulation can be in direct contact with the
scavenging layer, such as iron, or OMAC® that includes an
oxygen scavenger. In an aspect, the scavenger could be
added to the formulation as particles that are prevented from
getting instilled with eye drops by including barrier (e.g.,
filter) at the inlet to the tip as described further below.

Figure 5:
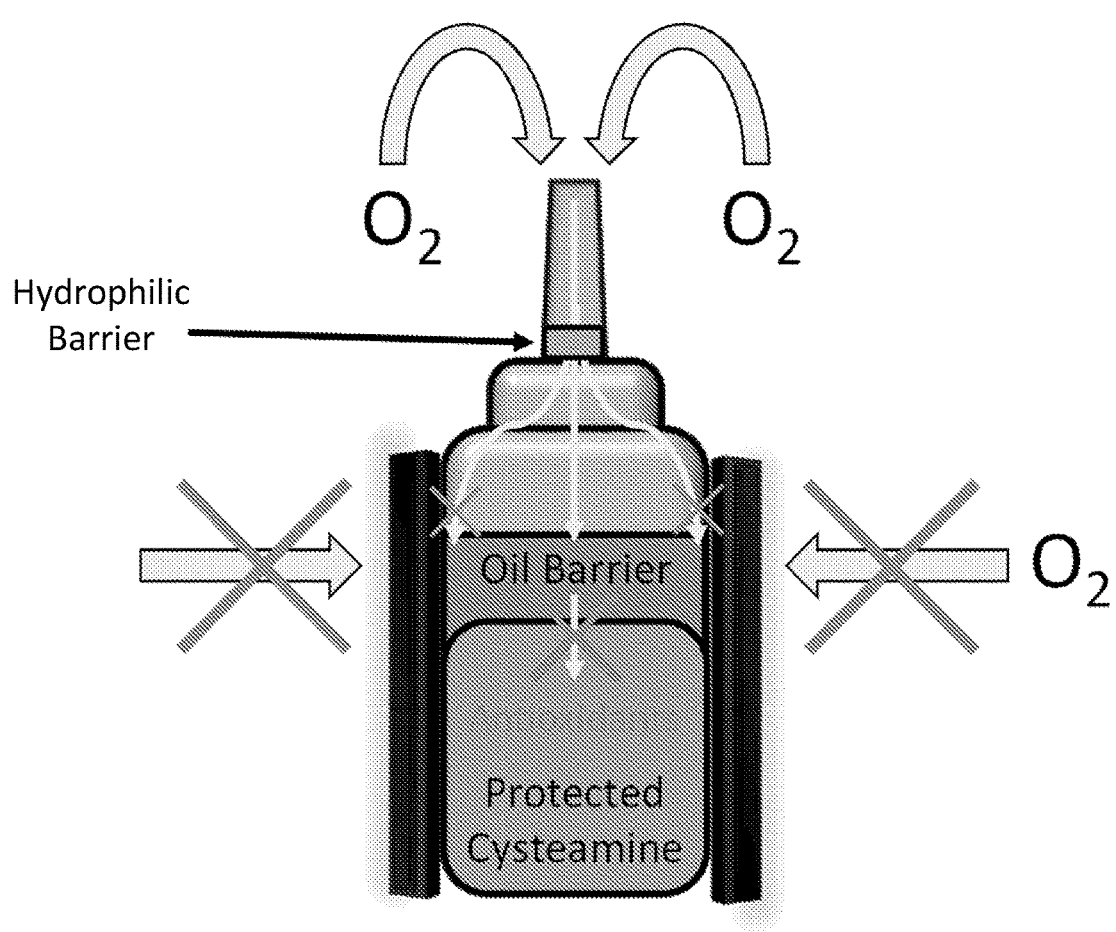

An aspect of the present disclosure can include a bottle
having a structure (e.g., a barrier) to reduce the amount of oil
that is ejected as the drop are created. For example, as the
amount of solution in the bottle decreases, the chance of oil
being ejected likely increases. In an aspect, the bottle can
include a design to ensure that the remaining oil and a small
fraction of the aqueous formulation cannot be instilled. This
can be accomplished by placing a barrier (e.g., a filter such
as a hydrophilic filter) near or in the tip of the bottle. For
example, FIG. 5 illustrates a hydrophilic barrier filter at the
bottom of the tip of the bottle. The hydrophilic filter will
allow easy flow of the aqueous formulation but block oil,
thus minimizing the possibility of dispensing oil drops or
aqueous drops with a substantial fraction of oil. Hydrophilic
filters can either be prepared from hydrophilic materials or
have hydrophilic coatings disposed on other materials that
form the barrier. In an aspect, the pore size of the hydrophilic
filters can be chosen to achieve a desired breakthrough
pressure for oils. If the breakthrough pressure is larger than
the typical pressure in the bottle during eye drop dispensing,
a patient will be unable to squeeze out the oil.

Figure 6:
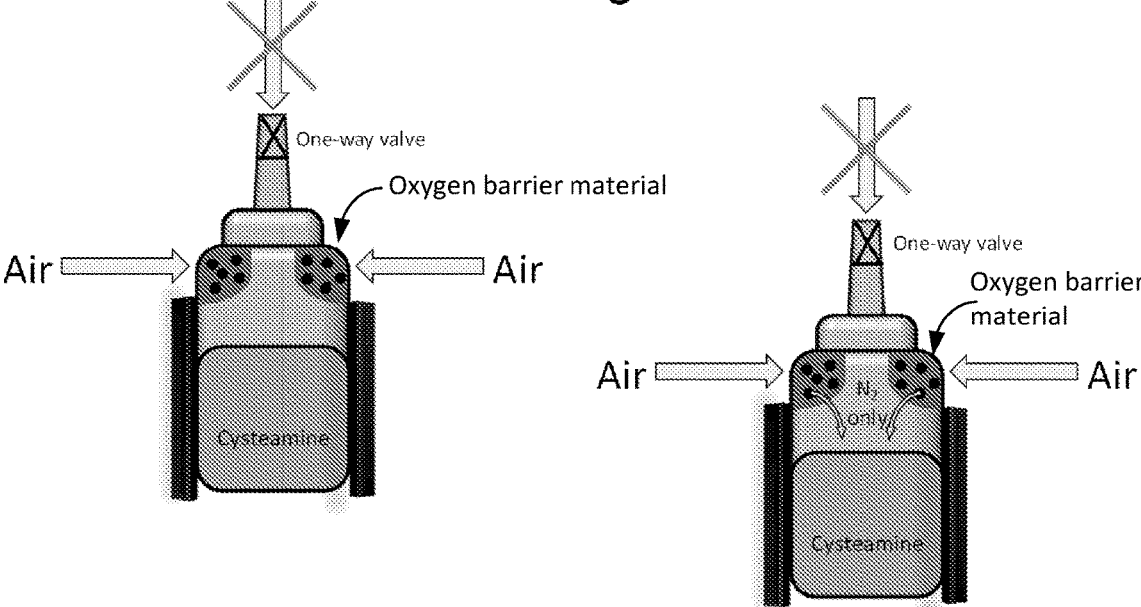

In another aspect, the bottle can be designed such that the
air entering from the top to replace the instilled drop contacts
the formulation only after the oxygen portion of the air is
scavenged. In an aspect, this can be accomplished by
incorporating a one way valve into the bottle tip to ensure
that the air cannot enter from the path through which the
drop is dispensed. Instead, air enters through a separate flow
path or channel that contains one or more of a structure,
chemical (e.g., oxygen blockers, scavengers, and the like) to
ensure that oxygen (e.g. as well as microorganisms) does not
contact the formulation, such as that shown in FIG. 6. This
design may also eliminate the need for use of preservatives
in the formulation because the microorganisms entering with
air will get blocked from contacting the formulation.

Another aspect of the present disclosure includes a prod-
uct including a contact lens holder with one or more drug
loaded contact lenses in a solution (e.g., such as those
described herein including an effective amount of cysteam-
ine or derivatives thereof to treat cystinosis). In an aspect,
the contact lens holder includes at least one barrier layer
(such as those described herein), where each of the barrier
layers reduces the amount of $O_2$ from entering the contact
lens holder as compared to a contact lens holder without the barrier layer. An aspect also includes that the space in the contact lens holder not including the contact lenses and the solution is occupied by a gas (e.g., $N_2$ or an inert gas) that is substantially free of $O_2$. As a result, the shelf life of the contact lenses can be extended.

In an additional embodiment, the one or more contact lens holders can be disposed within a container, where the environment with the container is substantially free of $O_2$ (e.g., $N_2$ or an inert gas). In an aspect, the container can include at least one barrier layer, where each of the barrier layers reduces the amount of $O_2$ from entering the container as compared to a container without the barrier layer. In this way, the shelf life of the contact lenses can be extended.

In an aspect, one or more of the various features can be combined or all of the features could be combined.

As described herein, the oxidation of the cysteamine can be reduced by one or more strategies. One strategy includes use of catalase in the solution to slow down oxidation of cysteamine, which can extend the use life by about 20 to 50% or more. Another strategy includes the use of an oil layer on top of the solution to reduce the diffusion of the $O_2$ in the environment in the bottle into the solution and when the oil is an antioxidant (e.g., vitamin E), the oil can further reduce the $O_2$ that diffuses into the solution. Yet another strategy includes uses a bottle that includes the composition, where the bottle includes one or more barrier layers (e.g., where the barrier layer can include ethylene vinyl alcohol (EVOH), aluminum foil, and an iron based absorbent layer) around the bottle so that $O_2$ diffusion is reduced. In addition, another strategy includes placing the bottle including the composition include a container, where the container includes one or more barrier layers to limit $O_2$ diffusion. One embodiment includes the use of two or more strategies, another embodiment includes use of three or more strategies, and another includes use of all of these strategies. These strategies have a synergistic impact on the reduction of $O_2$ entering the solution, for example, $O_2$ that enters the bottle and is in the headspace of the bottle will have a reduced diffusion rate into the solution through the oil layer so that the $O_2$ will competitively diffuse through the bottle wall and into the $O_2$ absorbent layer of the barrier layer. In this way, the $O_2$ diffusing into the solution reduced due to the synergistic interplay between the oil layer and the barrier layer.

These strategies can be used to address shelf life (e.g., use of barrier layers on the bottle and container as well as the low $O_2$ environment of each of the bottle and container) and strategies to address use life (e.g., catalase in the solution, oil layer, barrier layer on the bottle, and/or the low $O_2$ environment in the bottle). Embodiments of the present disclosure are advantageous in that they can significantly reduce the handling costs associated with compositions including cysteamine and also increase the time that these compositions can be effective.

Aspects of the present disclosure refer to storage of the composition in the bottle and the container. "Storage" refers to maintaining the composition or the ophthalmic composition under a set of physical conditions (e.g., room temperature) for a period of time (e.g., a month). For example, storage can include maintaining the composition or the ophthalmic composition at a particular temperature, humidity, or both (e.g., 25° C./60% RH) for a given duration (e.g., 4 weeks or longer). As used herein, "storage" can include, for example, storage by a manufacturer, a distributor, a pharmacy, or a hospital prior to dispensing the composition to a patient or health care provider. "Storage" can also include handling by a patient, where the patient maintains the composition or the ophthalmic composition under a set of physical conditions (e.g., room temperature) for a period of time (e.g., a month).

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

The aim of the present disclosure was to design a system that can increase the duration of use after opening from 1-week to 1-month while maintaining a neutral pHTwo different approaches were used.

1. Use of anti-oxidants—Cysteamine itself is considered an anti-oxidant, but a more potent scavenger could out-compete cysteamine for available oxygen or prevent the formation of an intermediary, such as hydrogen peroxide [23,24]. While powerful iron-based anti-oxidants exist, the pharmaceutical application requires that any used anti-oxidant be bio-compatible. Iron ions in solution have also been shown to catalyze the formation of free radicals, increasing the degradation rate of thiols [25]. The studies of the present example examine the effects of vitamin C and vitamin E, two naturally occurring anti-oxidants that also have great benefits to ocular health [26-29]. Vitamin C is highly hydrophilic and can be added directly to the aqueous solution at high concentration. Vitamin E has a very low solubility in aqueous formulations and can only be solubilized with the aid of a surfactant to form an emulsion. Emulsions have been shown to reduce oxygen transport and increase stability of other hydrophilic antioxidants [30]. Finally, the effect of the enzyme catalase is explored, which can revert peroxide species back to diatomic oxygen, potentially starving the system of radicals required to oxidize cysteamine.

2. Barrier to oxygen—Oxygen can reach the eye drop bottle via diffusion through the bottle surface and additionally with the air that is sucked in after dispensing the eye drop to equalize the pressure. Described are two different approaches to minimize oxidation from these two mechanisms.

Retardation of oxygen diffusion through the bottle—Diffusion of oxygen through the bottle can be reduced by either manufacturing a thicker bottle using materials that are resistant to oxygen diffusion, or alternatively coating the bottle with suitable materials. This approach has already been shown to be effective with Cystadrops®.

Insoluble oil layer as oxygen barrier—An eye drop bottle always contains air on top of the aqueous formulations, and the air fraction increases with use. The bottle is squeezed to dispense the drop and afterwards an equal volume of air enters the bottle to equalize the pressure. The oxygen that enters the bottle with this air can cause drug degradation. To slow down the reaction from this oxygen, an internal oxygen barrier was created in the bottle via a layer of oil that is insoluble with the formulation. The oil layer creates a barrier for oxygen transport from the air phase in the bottle into the formulation thereby reducing the degradation rates. The oil layer could also be used to store hydrophobic anti-oxidants, which could scavenge oxygen and prevent it from entering into the aqueous cysteamine solution. Described is a design including a two component drug formulation containing the aqueous drug formulation and an additional oily phase that is lighter than water so it will form a layer at the top of the formulation, thereby providing a barrier to oxygen diffusion. It is critical that the presence of this barrier does not impede the drop dispensing dynamics and the barrier oil is biocompatible.

With a combination of these two approaches, it should then be possible to create a system that meets a goal of maintaining >90% cysteamine one month after opening. During storage before opening, oxygen can only enter the formulation through the packaging. We then propose using the same material used as a diffusion barrier on the bottle to function as a secondary, sealed container that will allow us to reach our second main goal of one year shelf life, alleviating the need to freeze the formulations as in CYS-TARAN™.

Currently eye drops are the only approved ophthalmic vehicles for cystinosis therapy but other approaches are explored to increase the residence time in tears such as by using contact lenses [31, 32]. The proposed contact lenses are daily disposable so there is limited concern about degradation of the drug after opening. However, shelf life of the drug loaded contacts is critical and so we also test whether the drug loaded contact lenses can retain non oxidized drug after extended shelf life by using the OMAC® packaging to retard oxygen diffusion into the lens.

2.0 Materials and Methods

2.1 Materials

Cysteamine ($\geq 98\%$) was purchased from Fischer Scientific. Phosphate buffered saline, 1x without calcium and magnesium (PBS, pH=7.4) was purchased from Mediatech, Inc. Vitamin E ($\alpha$-tocopherol, $\geq 96\%$) was purchased from Sigma-Aldrich. Vitamin C (L-ascorbic acid, F.W.=176.13) was purchased from Fischer Scientific. Soybean oil was purchased from Spectrum (Gardena, CA). Tween 80 was purchased from Sigma-Aldrich. Sodium hydroxide ($\geq 97\%$) tablets were purchased from Sigma-Aldrich. Catalase (from bovine liver, 2000-5000 units/mg) was purchased from Sigma-Aldrich. Aluminum foil (18 $\mu$m thick) was purchased from FisherSci. OMAC® films were provided by Mitsubishi Gas Chemical America.

2.2 Methods for Reducing Drug Degradation 2.2.1 Anti-Oxidants

Table 1 lists the anti-oxidant containing formulations explored here. The formulations containing vitamin E and/or soybean oil (VE, SO, VESO) were prepared at solubility limit by adding excess of the hydrophobic components followed by centrifugation (Fisher Scientific Centrific™ Centrifuge) for 30 minutes. All formulations containing hydrophilic components (SUR, CAT) were prepared by stirring at room temperature till dissolution. All formulations were tested for pH and adjusted to 7.4 if required. For each formulation, 20 mL of liquid was placed into a 22 mL, flat bottom, 28 mm diameter, glass vial (Fisher Scientific). Each formulation was purged with nitrogen gas for two hours to minimize dissolved oxygen. After purging, 2.0±0.1 mg cysteamine was added to each formulation to achieve a concentration of 0.1 mg mL$^{-1}$ which is about one-fourth of the concentration in the commercial formulation. We are interested in the relative changes in degradation rates by addition of anti-oxidants so reducing concentration will not be a significant factor. An additional formulation (FORM) was prepared at the cysteamine concentration of CYST-ARAN™ of 4.4 mg mL$^{-1}$ to determine the effect of concentration. The vials were then left exposed to atmospheric oxygen to ensure that the degradation rates were not limited by availability of oxygen. The formulations were periodically sampled for measurement of UV spectra in 190-350 nm range (Thermo Scientific™ GENESYS™ 10S UV-Vis Spectrophotometer). The spectra of cysteamine and the oxidation product cystamine are sufficiently different so the combined spectra obtained from the samples can be separated via a least square fit to yield the concentrations of both components. After analyzing, the solution was returned to the vial to conserve total volume. The UV spectra measurements were conducted for 24 hours to determine the steady state degradation rate.

TABLE 1

| Composition and drug degradation rates in 4.4 mg mL$^{-1}$ and 0.1 mg mL$^{-1}$ formulations (pH = 7 and room temperature) containing anti-oxidants (n = 6). | | |
| --- | --- | --- |
| Identification | Formulation | Rate of degradation ($\mu$g/hr) |
| VC | 0.1 mg mL$^{-1}$ drug & 0.5 mg mL$^{-1}$ vitamin C in PBS | 523 ± 53 |
| FORM | 4.4 mg mL$^{-1}$ drug in PBS | 132 ± 15 |
| PBS | 0.1 mg mL$^{-1}$ drug in PBS | 126 ± 4 |
| VE | 0.1 mg mL$^{-1}$ drug & vitamin E at solubility limit in PBS | 122 ± 11 |
| SO | 0.1 mg mL$^{-1}$ drug & soybean oil at solubility limit in PBS | 120 ± 4 |
| VESO | 0.1 mg mL$^{-1}$ drug & oil and vitamin E at solubility limit in PBS | 111 ± 4 |
| SUR | 0.1 mg mL$^{-1}$ drug & 1% (w/w) surfactant in PBS | 112 ± 7 |
| EM | 0.1 mg mL$^{-1}$ drug in emulsion (4.5% oil + 4.5% VitE + 1% surfactant) | 101 ± 9 |
| CAT | 0.1 mg mL$^{-1}$ drug & 0.15% catalase | 58 ± 5 |

2.2.2 Barrier to Oxygen 2.2.2.1 Oil Barrier

To explore the effect of oil barriers on oxidation, 2 mL of oil was added to 20 mL of aqueous solution containing 0.1 mg mL$^{-1}$ drug. The formulation was placed into the 22 mL vials used in section 2.2.1 resulting in a 3-mm thick oil layer on top of the cysteamine formulation. The top surface of the oil film was exposed to air to ensure that the measurement of the reduction in the oxidation rates represented the barrier effect of the film. A syringe needle was used to pierce the hydrophobic layer and withdraw aqueous sample periodically for measurement by UV-vis spectrophotometry to determine cysteamine concentration.

The effect of oil barrier on oxygen transport into the cysteamine formulation can be modeled by solving mass transport of oxygen through the film coupled with the oxidation reaction in the formulation. The oxidation reaction is a multi-step process involving several intermediates but it can be assumed that the reaction is limited by oxygen concentration and so it is zero order in drug concentration and first order in oxygen concentration. Additionally, the overall transport can be separated into an initial lag phase during which oxygen concentration in the formulation is zero because of the time taken for the mass transfer boundary layer thickness to reach the oil thickness. In the initial lag phase we can write the following model, $$\frac{\partial c}{\partial t} = D\frac{\partial^2 c}{\partial x^2} \qquad (1)$$

where C is oxygen concentration, t is time, D is diffusivity, and x is distance in the direction of the membrane's thickness. This equation can be solved with the following boundary conditions $$C(x,0)=0 \qquad (2)$$

$$C(0,t)=C_{sol} \qquad (3)$$

$$C(x{\to}\infty,t)=0 \qquad (4)$$

The initial condition (Eq. 2) assumes that the oxygen concentration is negligible due to deoxygenation. The boundary condition at the surface assumes that the oxygen concentration in the oil layer at the top surface is equal to the solubility limit of oxygen in oil. The last boundary condition assumes that the concentration far from the top surface is zero because the mass transfer boundary layer has not breached the film. These boundary conditions allow for the use of similarity method to solve the differential equation to yielding the following solution $$\frac{C(x,t)}{c_{sol}} = \text{erfc}\left(\frac{x}{2\sqrt{Dt}}\right) \qquad (5)$$

This expression shows that the boundary layer thickness in the oil film at any time t scales as $\sqrt{Dt}$ and so the diffusivity of oxygen in oil can be estimated as $$D{\sim}L^2/t_L \qquad (6)$$

where L is thickness of the membrane, and $t_L$ is lag time during which cysteamine degradation is negligible. The thickness L of the hydrophobic layer was both measured with a ruler and calculated by dividing volume of hydrophobic material over cross sectional area of the inside of the vial and the lag time was determined from the degradation data.

At long times, the mass transfer through the hydrophobic barrier reaches a pseudo-steady state at which the concentration profile in the oil film is linear and the rate of transport is matched by the rate of consumption through the oxidation reaction, i.e., $$V\frac{dC}{dt} = -AJ \qquad (7)$$

where V is volume, C is concentration of cysteamine in solution, A is the area perpendicular to the direction of diffusion and J is the pseudo-steady flux through the film, $$J = \frac{Dc_{sol}}{L} \qquad (8)$$

where the concentration is the oil at the x=L is considered negligible because the reaction in the aqueous formulation is limited by oxygen transport. Since $c_{sol}$ is available in literature and D can be estimated from the lag phase, the rate of mass loss of cysteamine can be calculated and compared that to the experimental data. The model is useful in determining the minimum thickness of the oil layer that will increase the stability to the desired extent.

2.2.2.2 OMAC Film Barrier

Figure 2A:
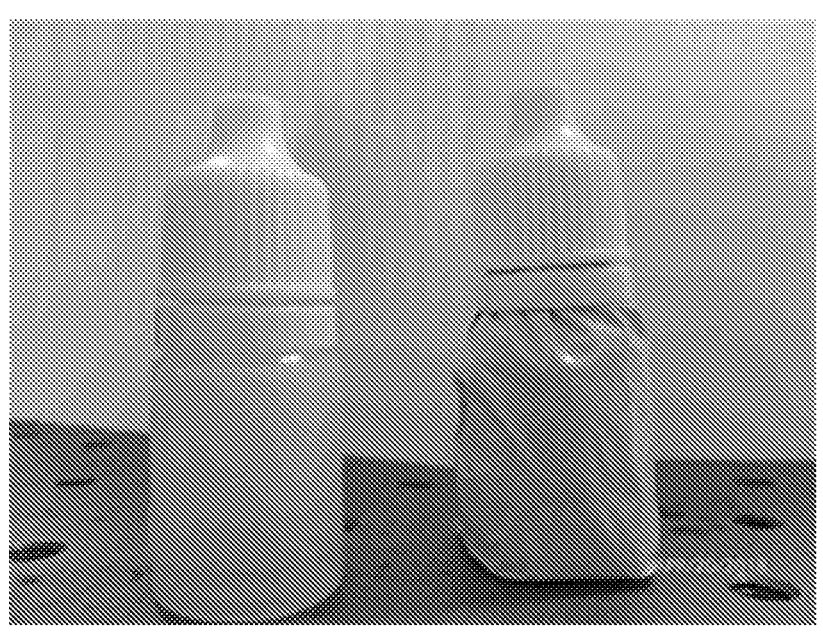
FIGS. 2A-2B show eye drop bottles.

The experiments described above were not required to be conducted in an eye drop bottle because the properties of the formulation and that of the film were being explored. To explore the effect of any alterations in packaging, it was considered more realistic to use a commercial eye drop bottle. Low density polyethylene eye drop bottles were purchased from Amazon.com and Ageless OMAC® (Mitsubishi Gas Chemical America, Inc) was used as the oxygen barrier. OMAC® is an oxygen resistant composite consisting of layers aluminum foil and iron-based absorbent layer [33]. The OMAC® was heat-sealed to the eye drop bottle using a hand iron (FIGS. 2A-2B), and additional layers of OMAC® were applied by the same approach. Samples were prepared with three layers (or 3×) of OMAC®. Prior to heat-sealing, the OMAC® sheets were left exposed for a month to fully oxidize the iron absorbent layer so that only the diffusive properties of the material would be analyzed. The caps for the OMAC® bottles were coated on the interior with aluminum foil to reduce oxygen diffusion when not eluting a drop The OMAC® coated eye drop bottles were filled with 5 mL of 0.44% drug in 1×PBS that was nitrogen purged for 2 hours, and capped to minimize evaporation. As these systems were in a nearly closed system, evaporation was not a concern, so they could be run for longer durations of time compared to the anti-oxidant experiments performed open to atmosphere. At certain time intervals, the screw cap was removed, and the bottle was squeezed to eject one drop. The mass of the drop was measured, and the drop was diluted 100 fold by PBS. This diluted solution was then measured by UV-vis spectrophotometry to determine the degradation of cysteamine.

As the oxygen permeability of many of these materials is well known, the degradation rate can be predicted using the following equation $$\text{Degradation rate} = \frac{P \cdot A}{\tau} * STP * \frac{\text{mol } RSH}{\text{mol } O_2} * mw_{RSH} \qquad (9)$$

where P is permeability, A is area (calculated as a cylinder to give a surface area of 13.85 cm$^2$), $\tau$ is thickness, STP is 22.4 L/mol, the stoichiometric ratio between cysteamine (RSH) and diatomic oxygen is 4, and the relative molecular mass of cysteamine is 77.15 g/mol. This equation can be used to determine the permeability of a material based upon the degradation of cysteamine.

2.2.2.3. Combined Approach

Bottles were manufactured with the 3× OMAC® as described in the previous section. Catalase (0.15%) was added to the cysteamine solution, which was nitrogen purged for an additional half hour. The solution was then placed in the bottle and topped with a 1.0 cm layer of 50% (v/v) soybean oil and 50% vitamin E. The bottle was then capped and tested for degradation of cysteamine while periodically withdrawing eye drop samples, as described in section 2.2.2.2.

2.3 Eye Drop and Contact Lens Packaging Before Opening

Figure 2B:

LDPE eye drop bottles were filled with 5 mL of 0.44 mg mL$^{-1}$ of cysteamine/PBS. These bottles were then placed in pouches of OMAC®—which had been made by folding the material on itself and heat-sealing three sides. Other bottles were placed into foil heat-sealable packs (Amazon). Both pouches are shown in FIG. 2B. After 25 days, these pouches were opened. The bottles were then tested by eluting a single drop and measuring for cysteamine degradation using UV-vis analysis.

ACUVUE® OASYS® lenses (Senofilcon A, diopter −3.50) were placed in CyroELITE™ Cryogenic Vials (Wheaton Science Products, polypropylene) filled with 5 mL of 25 mg mL$^{-1}$ drug solution. The drug concentration was chosen to achieve a desired mass of drug loading in the contact lens. Certain vials were then placed in pouches of OMAC®. Other vials were placed into foil heat-sealable packs (Amazon). Nitrogen gas was blown into the envelope for 5 minutes, and then the remaining open end was heat-sealed to close the vial. Lenses were then stored in a closed drawer and opened after 50 days for testing. Upon opening, the lenses were removed from the solution, dabbed with a Kimwipe to remove excess liquid on the surface, and then placed into 3 mL of fresh PBS, which had been purged for 1 hour. ACUVUE® OASYS® releases cysteamine in less than ten minutes once inserted into solution [33]. At this time point, a sample of the PBS was removed and analyzed with UV-vis spectrophotometry to determine the concentration of cysteamine, which was then used to calculate the fractional degradation after 50 days of storage.

3.0 Results

3.1 Stability of Aqueous Cysteamine in Formulations

The profile of cysteamine degradation are shown in FIG. 1A as a plot of the transient mass of cysteamine in the solution with time. The decrease in concentration is due to oxidation of cysteamine to cystamine. Table 1 lists the average degradation rates of the various formulations with antioxidants, which were obtained from the linear-slope fit of the mass of cysteamine in solution (FIG. 1A). Degradation rates are comparable for most formulations except CAT which degraded at only about 58% of the control rate.

3.2 Hydrophobic Barrier to Oxygen

Figure 1B:
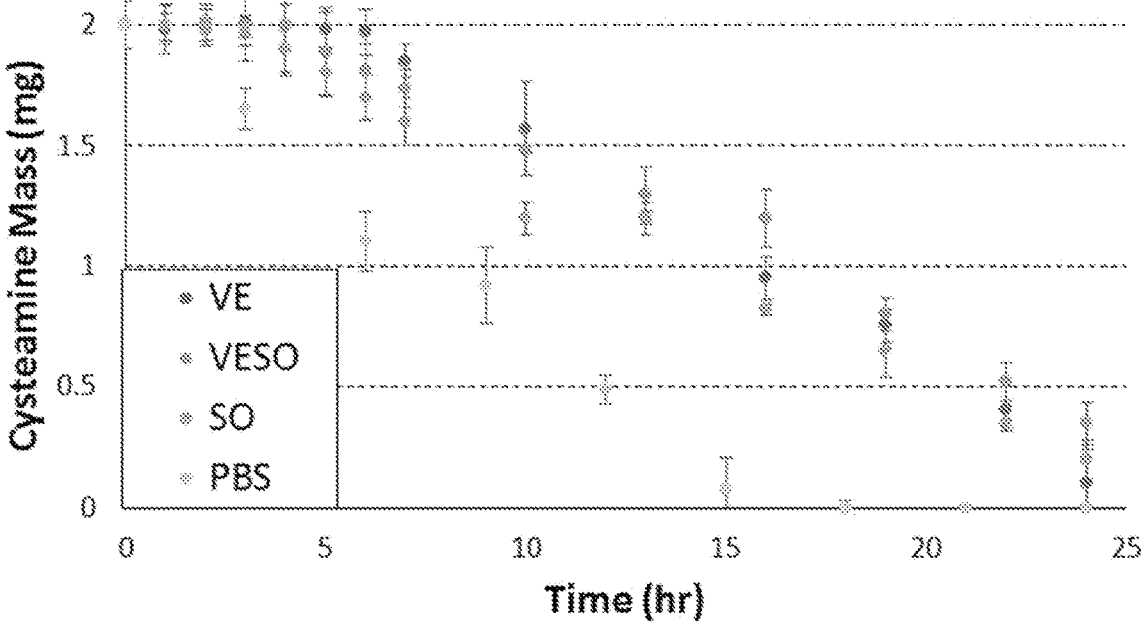
(FIG. 1B) 0.01% cysteamine oil layer formulations.

The profile of cysteamine degradation are shown in FIG. 1B. Table 2 lists the average degradation rates of the formulation covered with 3-mm thick hydrophobic layers and the predicted degradation rates for a 1-cm thick film. The vitamin E layer provided a lag of over six hours and a rate of degradation of 99 μg mL$^{-1}$. Soybean oil had a lag of about three-and-a-half hours and a rate of degradation of 82 μg mL$^{-1}$. The mixed hydrophobic layer had a delay of nearly four-and-a-half hours and a degradation time of 83 μg mL$^{-1}$, nearly identical to the rate of pure soybean oil.

3.3 Oxygen Resistant Packaging

Results for cysteamine degradation in eye drop bottles are shown in FIG. 10. This figure show a plot of the ratio of the cysteamine concentration at any time and the initial concentration. The formulation packaged in the unmodified bottle oxidized significantly in about 48 hours compared to about 170 hours for OMAC® covered bottles. The time for complete degradation was 350 and 1300 hours for the unmodified and OMAC® covered bottles, respectively. The formulation in 3× OMAC® bottles exhibited a minimal degradation until about 800 hours, with complete degradation occurring in 1800 hours. A fit to the linear region gives a cysteamine degradation of 0.0617 mg/hr for the control LDPE bottle, 0.0270 mg/hr for a single layer of OMAC®, and 0.0155 mg/hr for 3× OMAC®. All of these rates are much lower than the measured degradation rate of cysteamine in PBS exposed to atmosphere. FIG. 10 also shows that the addition of a hydrophobic layer of vitamin E and soybean oil reduces the degradation rates further.

3.4 Storage Packaging for Eye Drop Bottles and Contact Lenses

Results for cysteamine eye drop bottles after 25 days of storage are shown in Table 3. The formulation in control LDPE bottles degraded 43.1%±5.6, while that in the foil and OMAC® packets degraded 0.8%±2.1% and 0.5%±1.6%, respectively. Results for cysteamine contact lenses after 50 days of storage are also shown in Table 3. The drug in the control lenses degraded 77.6%±3.1%, while those in the foil and OMAC® packets degraded 21.9%±4.1% and 6.0%±2.1%, respectively.

TABLE 2

Effect of hydrophobic layer on cysteamine (0.1 mg mL$^{-1}$ in PBS) degradation (n = 6). The oil layers on top of the aqueous formulation are 3.0 ± 0.1 mm thick.

| Barrier Formulation | Measured degradation rate (μg/hr) | Measured delay (hr) | Calculated O$_2$ diffusivity (m$^2$/s) | Calculated degradation rate (μg/hr) |
|---|---|---|---|---|
| Vitamin E | 99 ± 13 | 6.3 ± 0.2 | 5.16E−10[1] | 84 |
| Vitamin E, Soybean Oil | 83 ± 9 | 4.4 ± 0.1 | 7.71E−10 | 79 |
| Soybean Oil | 82 ± 6 | 3.6 ± 0.2 | 9.36E−10[1] | 73 |

| Barrier Formulation | Calculated degradation rate (μg/hr) for 1 cm thick barrier | Delay in degradation (hr) for 1 cm thick barrier |
|---|---|---|
| Vitamin E | 29 | 53.8 |
| Vitamin E, Soybean Oil | 27 | 35.9 |
| Soybean Oil | 26 | 29.7 |

[1]Hydrophobic oils generally fall in the range of 1.1E−9 to 7E−10 m$^2$/s, with soybean oil having a literature value of 8.70E−10 m$^2$/s [40]

TABLE 3

| Drug degradation in packaged eye drop bottles and contact lenses stored at room temperature (n = 3) | | | | |
|---|---|---|---|---|
| Eye Drop Bottles (Low Density Polyethylene bottles) | | | | |
| 25 Days | Percent Degradation | Degraded cysteamine (mg) | Degradation Rate (µg/day) | Predicted Days Until 10% Degradation |
| Control | 43.1% ± 5.6% | 9.482 | 379.9 | 6 |
| Aluminum Foil | 0.8% ± 2.1% | 0.176 | 7.0 | 313 |
| OMAC ® | 0.5% ± 1.6% | 0.110 | 4.4 | 500 |

1 - Total Mass = 22.0 ± 0.1 mg cysteamine

| Contact Lenses (Polypropylene containers) | | | | |
|---|---|---|---|---|
| 50 Days | Percent Degradation | Degraded cysteamine (µg) | Degradation Rate (µg/day) | Predicted Days Until 10% Degradation |
| Control | 78.4% ± 3.1% | 314.0 | 78.4 | 57 |
| Aluminum Foil | 20.9% ± 4.1% | 83.7 | 1.67 | 215 |
| OMAC ® | 6.0% ± 2.7% | 24.0 | 0.48 | 750 |

1 - Total Mass = 400 ± 15 µg cysteamine

4.0 Discussion

4.1 Degradation of Cysteamine

Cysteamine is a thiol which makes it highly reactive with oxygen giving it the ability to protect other sensitive molecules from oxidation and radiation [25]. The reaction mechanisms are complex as cysteamine reacts with intermediate radicals formed from oxygen, which are called reactive oxygen species, with the following overall equation $$2NH_3C_2H_4SH+0.5O_2 \rightarrow NH_3C_2H_4SSC_2H_4NH_3+H_2O$$

For ambient conditions, oxygen will likely be the limiting factor, both due to solubility and diffusivity. As oxygen is the limiting reactant, observed degradation of cysteamine is zero order with respect to cysteamine concentration on the time scale of these experiments. Similar behavior is observed for other antioxidants under similar conditions [34]. The zero order rate implies that the concentration of cysteamine should decrease linearly with time, so the degradation rate can be measured by determining slope of the collected data. This assumption is validated by the results in Table 1 which compare the degradation rate of 4.4 mg mL$^{-1}$ of cysteamine (132±15 µg/hr) to that of 0.1 mg mL$^{-1}$ (126±4 µg/hr).

4.2 Effects of Anti-Oxidants on Degradation of Cysteamine in Aqueous Solution

4.2.1 Hydrophilic Anti-Oxidants

Vitamin C is highly hydrophilic and so can be dissolved into cysteamine solutions at high concentration. Vitamin C is less reactive than cysteamine so its concentration must be much higher to out-compete the drug for oxygen. Unfortunately, vitamin C increased the degradation rate of cysteamine, which has been observed in other cases and attributed to regeneration of the oxidized vitamin C [35],[36]. Studies reported in literature suggest that typical anti-oxidants cannot outcompete cysteamine so it would be difficult to stabilize the cysteamine formulation by adding soluble anti-oxidants in spite of the higher concentration.

4.2.2 Hydrophobic Anti-Oxidants and Emulsions

The combination of vitamin E and soybean oil had a noticeable decrease in cysteamine degradation to a rate of 111±4 µg/hr. The surfactant Tween 80 also caused a reducing in the rate to 112±7 µg/hr. Combining the oil and the surfactant into an emulsion formulation resulted in a further decrease to 101±9 µg/hr. This decrease though is not sufficient to achieve the desired increase in shelf life.

4.2.3. Enzymes

Catalase is an enzyme that catalyzes the decomposition of hydrogen peroxide to diatomic oxygen and water. While diatomic oxygen is a reactant for the oxidation of cysteamine, it most likely must first form a peroxide or superoxide [37]. Previous work has shown that the addition of catalase can decrease the oxidation of cysteamine in PBS with 5-10% calf serum [38]. Catalase has a more noticeable reduction in cysteamine oxidation rate compared to other formulations, nearly halving the degradation rate to 58±5 µg/hr. While catalase does decrease the degradation rate by nearly half, it is not enough on its own to reach the desired month-long shelf life.

4.3 Use of Hydrophobic Materials as Barriers to Oxygen

Results in Table 2 show significant benefit of using oils to act as barriers to oxygen. The benefit of delayed degradation is not significant for either the 3-mm or 1-cm film in comparison to the desired shelf like of a month but the decrease in pseudo-steady oxidation rate by about 20-30% is significant. The estimated value of diffusivity of oxygen in soybean oil based on fitting the experimental lag to the model is in reasonable agreement with reported values in literature and the predicted degradation rate is in reasonable agreement with the measured values, further validating the model. Based on the model, increasing the oil film thickness to 1-cm will increase the lag time to about 50 hrs for vitamin E and decrease the degradation rate to about 21% of the control (Table 2). In order to examine the practicality of a hydrophobic barrier layer, a cysteamine solution with a 1 cm vitamin E layer was placed into an eye drop bottle (FIGS. 3A-3C). A drop was dispensed and analyzed using UV-vis spectrophotometry. As seen in FIGS. 3A-3C, the density differences between the aqueous phase and vitamin E lead to rapid migration of vitamin E towards the top when the bottle is inverted for dispensing. UV analysis of the eluting drop shows that the concentration of the drug is unchanged. This example shows that the proposed concept of introducing a hydrophobic barrier could be viable as it does not interfere with the drop dispensing. This approach will however need additional testing to ensure that under normal patient use the ejected drop does not contain any undissolved oil. This issue will probably become more critical after a majority of the aqueous formulation is dispensed. Thus, the bottle design may need to be modified to ensure that the remaining oil and a small fraction of the aqueous formulation cannot be instilled, as can be envisioned by one of ordinary skill in the art.

4.4 Effect of OMAC Packaging

The permeability of low density polyethylene (LDPE) to oxygen is about $4 \times 10^{-8}$ $(cm^3)cm/s/cm^2/atm$. A literature review shows that many other plastics are less permeable to oxygen including a commonly used material polyvinylchloride (PVC) that has a permeability of $4 \times 10^{-10}$ $(cm^3)cm/s/cm^2/atm$. Materials such as ethylene vinyl alcohol (EVOH) have an even lower oxygen permeability of about $8 \times 10^{-13}$ $(cm^3)cm/s/cm^2/atm$ [39]. Using any of these low permeability materials as coatings or as the materials for making the bottle will likely improve the stability of the cysteamine formulation. The OMAC® material that is tested here is likely a better option because it is marketed to have a lower oxygen permeability than EVOH and the difference may be higher for the eye drop bottle application because the permeability of EVOH increases when it is wet. The OMAC® barrier can be further beneficial through the oxygen scavenging layer though that effect is not explored here.

Figure 1C:
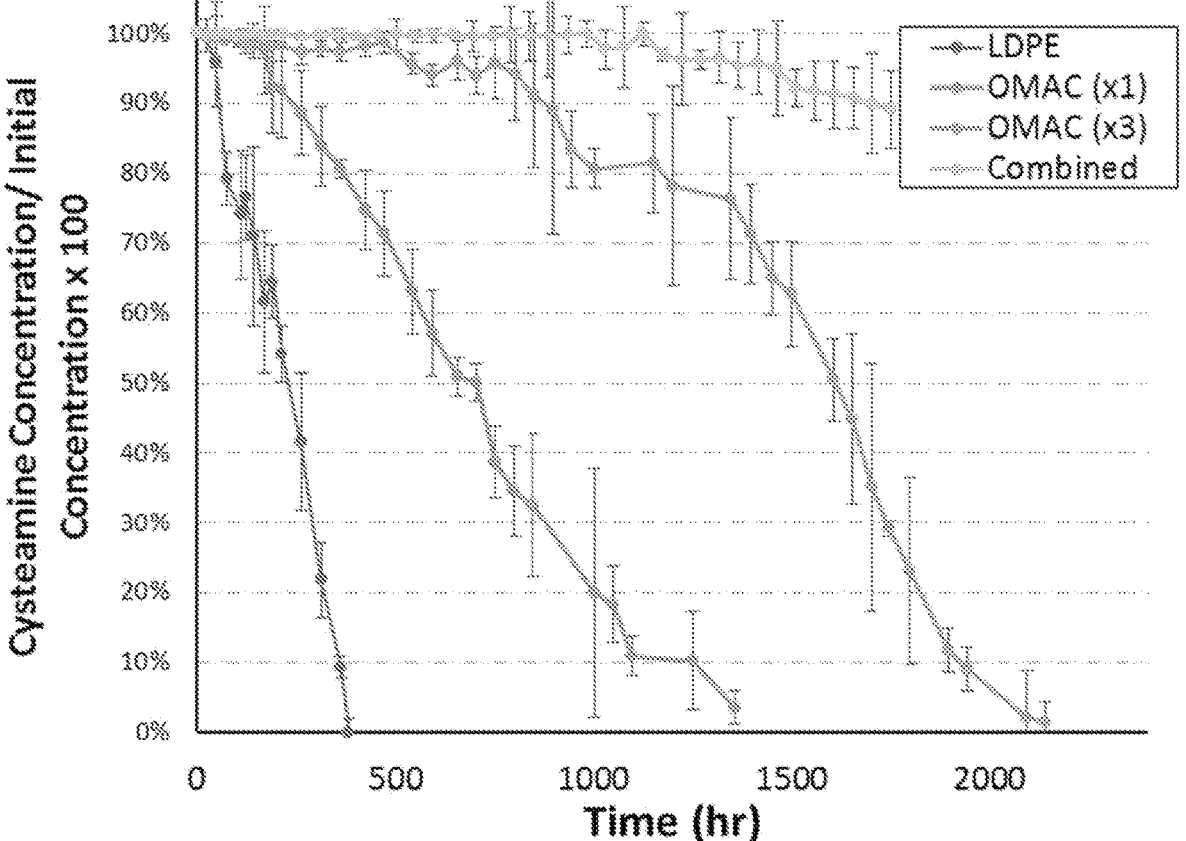

FIG. 1Cc shows that addition of OMAC® both delays and slows down the rate of cysteamine oxidation from about 60 µg cysteamine/hr for the LDPE bottle to 27 and 15 µg/hr for bottles covered with one and three layers of OMAC®, respectively. Based on the measured degradation rates, the average oxygen permeability of OMAC® was determined to be $7.8 \times 10^{-13}$ $(cm^3)cm/s/cm^2/atm$.

While OMAC® decreases the oxidation rates, it is surprising that three layers led to less than three-fold reduction compared to the single layer. The less than proportional decrease is likely due to the air that enters the bottle to replace the instilled drop. Each dispensed drop is 30 µL in volume, which implies that air of equal volume enters the bottle after drop dispensing to equalize pressure. At STP, $3 \times 10^{-7}$ mol of $O_2$ enter the bottle after each drop, which would react with $1.2 \times 10^{-8}$ moles of cysteamine. Each eye drop bottle contains $3.2 \times 10^{-4}$ moles of cysteamine, suggesting that each drop should react 0.4% of the total cysteamine to give a rate of roughly 10 µg/hr for these experiments. This matches the degradation rate of OMAC®×3, suggesting that nearly the entire degradation is due to air entering the bottle. A recalculation of the permeability after subtracting the 10 µg/hr degradation from the data for the sample with a single OMAC® layer yields an average permeability of $4.9 \times 10^{-13}$ $(cm^3)cm/s/cm^2/atm$, which indeed is significantly lower than EVOH. It is noted that the rate of eye drop instillation in our experiments was significantly lower than that in clinical use, which is about 8 times a day. The higher number of drops instilled will result in faster degradation.

4.5 Combined Approach

The three approaches of including catalase in the formulation, and placing the oil and the OMAC® (×3) barriers were jointly examined to determine whether the benefits of each approach can be combined to achieve the targeted stability. As seen in FIG. 1C, the drug concentration was about 90% of the starting value after two months of opening the bottle, showing that both catalase and the hydrophobic layer add to the benefits of the OMAC® layer.

4.6 Eye Drop Bottle and Contact Lens Packaging

Eye drop bottles stored in the aluminum and OMAC® pouches retained >98% of the cysteamine after 25 days. This high stability shows that keeping the eye drops bottles in an external pouch should easily eliminate the need to ship cysteamine frozen. Using the 25 day results to calculate the degradation rate suggest both packages will provide a year of shelf life at room temperature.

Contact lenses packaged in the lab-made OMAC® pouches retained ~95% of cysteamine after 50 days (Table 3). While one reason for this increased stability is a higher drug concentration-25 mg $mL^{-1}$ compared to 5 mg $mL^{-1}$ in eye drop bottles, the difference between the control and the OMAC® covered samples shows that on this time scale, diffusion barriers to oxygen will extend the stability of cysteamine in a sealed container to months. The small amount of degradation for OMAC® samples suggests that the majority of its degradation was due to oxygen still present in the system that did not escape during nitrogen purging. Aluminum foil would be expected to have a similar oxygen resistance compared to the OMAC®; however, a 20.9±4.1% degradation was still observed.

Both of these examples show that keeping cysteamine in a secondary sealed container that is a barrier to oxygen can significantly improve stability at room temperature.

5.0 Conclusion

Addition of common antioxidants had either adverse or insignificant effect on preventing the oxidation of cysteamine, except catalase, which reduced the degradation rate by nearly 58%. Using oil layer on top of the formulation as an oxygen-barrier reduced oxidation rates significantly. However, oxygen resistant packaging material OMAC® showed the most promising results for minimizing drug degradation through blocking diffusion of oxygen into the bottle. In fact, there is negligible degradation for about a month. Subsequently, oxygen ingress after drop dispensing contributed to some degradation. Using OMAC® with an oxygen scavenging layer and/or including oil layer in the formulation can further reduce oxygen from the ingress of air. Both eye drops and contact lenses packaged in OMAC® pouches also retained drug stability due to a significant reduction in oxygen diffusion and are predicted to be stable for over a year. A combination of multiple approaches is considered here—a sealed pouch for storage until use, a bottle/blister pack layered with oxygen resistant material, a hydrophobic layer to reduce the effect of air entering the eye drop bottle, and catalase in the aqueous solution, should ensure the stability of cysteamine for a month after opening, which would be a significant improvement over current formulation.

EXAMPLE 1 REFERENCES

[1] Gahl, W A, N Bashan, F Tietze, I Bernardini, and J D Schulman. "Cystine Transport Is Defective in Isolated Leukocyte Lysosomes from Patients with Cystinosis." *Science* 217, no. 4566 (Sep. 24, 1982): 1263. https://doi.orq/10.1126/science.7112129.

[2] Gahl, William A., Ernest M. Kuehl, Fumino Iwata, Anne Lindblad, and Muriel I. Kaiser-Kupfer. "Corneal Crystals in Nephropathic Cystinosis: Natural History and Treatment with Cysteamine Eyedrops." *Molecular Genetics and Metabolism* 71, no. 1 (Sep. 1, 2000): 100-120. https://doi.org/10.1006/mgme.2000.3062.

[3] Bishop, Rachel. "Ocular Complications of Infantile Nephropathic Cystinosis." *The Journal of Pediatrics* 183 (Apr. 1, 2017): S19-21. https://doi.org/10.1016/j.j-peds.2016.12.055.

[4] Liang, Hong, Christophe Baudouin, Rachid Tahiri Joutei Hassani, Francoise Brignole-Baudouin, and Antoine Labbe. "Photophobia and Corneal Crystal Density in Nephropathic Cystinosis: An In Vivo Confocal Microscopy and Anterior-Segment Optical Coherence Tomography Study." *Investigative Ophthalmology & Visual Science* 56, no. 5 (May 21, 2015): 3218-25. https://doi.org/10.1167/iovs.15-16499.

[5] Nesterova, Galina, and William Gahl. "Nephropathic Cystinosis: Late Complications of a Multisystemic Disease." *Pediatric Nephrology* 23, no. 6 (Jun. 1, 2008): 863-78. https://doi.org/10.1007/s00467-007-0650-8.

[6] Jones, N. P., R. J. Postlethwaite, and J. L. Noble. "Clearance of Corneal Crystals in Nephropathic Cystinosis by Topical Cysteamine 0.5%." *British Journal of Ophthalmology* 75 (1991): 311-12.

[7] Kaiser-Kupfer, Muriel I., Maria A. Gazzo, Manuel B. Datiles, Rafael C. Caruso, Ernest M. Kuehl, and William A. Gahl. "A Randomized Placebo-Controlled Trial of Cysteamine Eye Drops in Nephropathic Cystinosis." *Archives of Ophthalmology* 108, no. 5 (May 1, 1990): 689-93. https://doi.org/10.1001/ar-chopht.1990.01070070075038.

[8] "CYSTARAN." http://cystaran.com/.

[9] https://www.accessdata.fda.gov/drucisatfda docs/nda/2012/2007400rici1s000MedR.pdf

[10] http://www.ema.europa.eu/docs/en GB/document library/EPAR-Product Information/human/003769/WC500221981.pdf

[11] Radojkovic, Branko. (2015). Cysteamine eye drops in the treatment of cystinosis—an Australian perspective. Journal of Pharmacy Practice and Research. 45. 440-445.

[12] Reda A. et al. (2017) Effect of Storage Conditions on Stability of Ophthalmological Compounded Cysteamine Eye Drops. In: JIMD Reports. Springer, Berlin, Heidelberg

[13] Biaglow, John E., Rolf W. Issels, Leo E. Gerweck, Marie E. Varnes, Birgit Jacobson, James B. Mitchell, and Angelo Russo. "Factors Influencing the Oxidation of Cysteamine and Other Thiols: Implications for Hyperthermic Sensitization and Radiation Protection." *Radiation Research* 100, no. 2 (Nov. 1, 1984): 298-312. https://doi.org/10.2307/3576351.

[14] Svensson, B. E. "Abilities of Peroxidases to Catalyse Peroxidase-Oxidase Oxidation of Thiols." *Biochemical Journal* 256, no. 3 (Dec. 15, 1988): 757-62. https://doi.orq/10.1042/bj2560757.

[15] Iwata, Fumino, Ernest M. Kuehl, George F. Reed, Lessie M. McCain, William A. Gahl, and Muriel I. Kaiser-Kupfer. "A Randomized Clinical Trial of Topical Cysteamine Disulfide (Cystamine) versus Free Thiol (Cysteamine) in the Treatment of Corneal Cystine Crystals in Cystinosis." *Molecular Genetics and Metabolism* 64, no. 4 (Aug. 1, 1998): 237-42. https://doi.orq/10.1006/mcime.1998.2725.

[16] Labbé, Antoine, Christophe Baudouin, Georges Deschenes, Chantal Loirat, Marina Charbit, Genevieve Guest, and Patrick Niaudet. "A New Gel Formulation of Topical Cysteamine for the Treatment of Corneal Cystine Crystals in Cystinosis: The Cystadrops OCT-1 Study." *Molecular Genetics and Metabolism*, Program and Abstracts for the 2014 Meeting of the Society for Inherited Metabolic Disorders, 111, no. 3 (Mar. 1, 2014): 314-20. https://doi.org/10.1016/j.ymgme.2013.12.298.

[17] Huynh, Nancy, William A Gahl, and Rachel J Bishop. "Cysteamine Ophthalmic Solution 0.44% for the Treatment of Corneal Cystine Crystals in Cystinosis." *Expert Review of Ophthalmology* 8, no. 4 (August 2013): 341-45. https://doi.org/10.1586/17469899.2013.814885.

[18] Lim, Lik Thai, Elliott Y. Ah-kee, and Cian E. Collins. "Common Eye Drops and Their Implications for pH Measurements in the Management of Chemical Eye Injuries." *International Journal of Ophthalmology* 7, no. 6 (Dec. 18, 2014): 1067-68. https://doi.orq/10.3980/j.issn.2222-3959.2014.6.29.

[19] Bozdag, Sibel, Koray Gumus, Özlem Gümüş, and Nurşen Ünlü. "Formulation and in Vitro Evaluation of Cysteamine Hydrochloride Viscous Solutions for the Treatment of Corneal Cystinosis." *European Journal of Pharmaceutics and Biopharmaceutics* 70 (Sep. 1, 2008): 260-69. https://doi.orq/10.1016/i.eipb.2008.4.10.

[20] Antoine Labbé, Christophe Baudouin, Georges Deschenes, Chantal Loirat, Marina Charbit, Geneviève Guest, Patrick Niaudet, A new gel formulation of topical cysteamine for the treatment of corneal cysteine crystals in cystinosis: The Cystadrops OCT-1 study, Molecular Genetics and Metabolism, Volume 111, Issue 3, 2014, Pages 314-320, ISSN 1096-7192,

[21] Sibel Bozdağ, Koray Gümüş, Özlem Gümüş, Nurşen Ünlü, Formulation and in vitro evaluation of cysteamine hydrochloride viscous solutions for the treatment of corneal cystinosis, European Journal of Pharmaceutics and Biopharmaceutics, Volume 70, Issue 1, 2008, Pages 260-269, ISSN 0939-6411, https://doi.orq/10.1016/j.e-jpb.2008.4.10.

[22] K Makuloluwa, Achini & Shams, Fatemeh. (2018). Cysteamine hydrochloride eye drop solution for the treatment of corneal cysteine crystal deposits in patients with cystinosis: An evidence-based review. Clinical Ophthalmology. Volume 12. 227-236. 10.2147/OPTH.S133516.

[23] Quijano, Celia, Beatriz Alvarez, Reynaldo M. Gatti, Ohara Augusto, and Rafael Radi. "Pathways of Peroxynitrite Oxidation of Thiol Groups." *Biochemical Journal* 322, no. 1 (February 1997): 167-73. https://doi.org/10.1042/bj3220167.

[24] Luo, Dayong, Scott W. Smith, and Bradley D. Anderson. "Kinetics and Mechanism of the Reaction of Cysteine and Hydrogen Peroxide in Aqueous Solution." *Journal of Pharmaceutical Sciences* 94, no. 2 (February 2005): 304-16. https://doi.org/10.1002/jps.20253.

[25] Kachur, Alexander V., Cameron J. Koch, and John E. Biaglow. "Mechanism of Copper-Catalyzed Oxidation of Glutathione." *Free Radical Research* 28, no. 3 (Jan. 1, 1998): 259-69. https://doi.org/10.3109/10715769809069278.

[26] Christen, William G, J. Michael Gaziano, and Charles H Hennekens. "Design of Physicians' Health Study II—A Randomized Trial of Beta-Carotene, Vitamins E and C, and Multivitamins, in Prevention of Cancer, Cardiovascular Disease, and Eye Disease, and Review of Results of Completed Trials." *Annals of Epidemiology* 10, no. 2 (Feb. 1, 2000): 125-34. https://doi.org/10.1016/S1047-2797(99)00042-3.

[27] [27] Bursell, S E, A C Clermont, L P Aiello, L M Aiello, D K Schlossman, E P Feener, L Laffel, and G L King. "High-Dose Vitamin E Supplementation Normalizes Retinal Blood Flow and Creatinine Clearance in Patients with Type 1 Diabetes." *Diabetes Care* 22, no. 8 (August 1999): 1245-51. https://doi.org/10.2337/diac-are.22.8.1245.

[28] Padayatty, Sebastian J., Arie Katz, Yaohui Wang, Peter Eck, Oran Kwon, Je-Hyuk Lee, Shenglin Chen, et al. "Vitamin C as an Antioxidant: Evaluation of Its Role in Disease Prevention." *Journal of the American College of Nutrition* 22, no. 1 (Feb. 1, 2003): 18-35. https://doi.org/10.1080/07315724.2003.10719272.

[29] Christen, William G., Robert J. Glynn, and Charles H. Hennekens. "Antioxidants and Age-Related Eye Disease Current and Future Perspectives." *Annals of Epidemiology* 6, no. 1 (Jan. 1, 1996): 60-66. https://doi.org/10.1016/1047-2797(95)00094-1.

[30] Coupland, John N., and D. Julian McClements. "Lipid Oxidation in Food Emulsions." *Trends in Food Science & Technology* 7, no. 3 (Mar. 1, 1996): 83-91. https://doi.org/10.1016/0924-2244(96)81302-1.

[31] Hsu, Kuan-Hui, Richard C. Fentzke, and Anuj Chauhan. "Feasibility of Corneal Drug Delivery of Cysteamine Using Vitamin E Modified Silicone Hydrogel Contact Lenses." *European Journal of Pharmaceutics and Biopharmaceutics* 85, no. 3, Part A (Nov. 1, 2013): 531-40. https://doi.orq/10.1016/j.ejpb.2013.4.017.

[32] Dixon Phillip, Fentzke, Richard C, Bhattacharya, Arnab, Konar, Aditya, Hazra, Sarbani, Chauhan, Anuj. "In vitro drug release and in vivo safety of vitamin E and cysteamine loaded contact lenses." *Internation Journal of Pharmaceutics* (2017) doi: 10.1016/j.ijpharm.2017.11.059

[33] "AGELESS OMAC®.". http://ageless.mqc-a.com/product/ageless-OMAC/.

[34] Sapei, Lanny, and Lie Hwa. "Study on the Kinetics of Vitamin C Degradation in Fresh Strawberry Juices." *International Conference and Workshop on Chemical Engineering UNPAR* 2013 (ICCE UNPAR 2013) 9, no. Supplement C (Jan. 1, 2014): 62-68. https://doi.org/10.1016/j.proche.2014.5.008.

[35] Chan, A. C. "Partners in Defense, Vitamin E and Vitamin C." *Canadian Journal of Physiology and Pharmacology* 71, no. 9 (September 1993): 725-31.

[36] Poljsak B, Raspor P. The antioxidant and pro-oxidant activity of vitamin C and trolox in vitro: a comparative study. J Appl Toxicol. 2008 March; 28(2) 183-8

[37] Zeida, Ari, Ryan Babbush, Mariano C. Gonzalez Lebrero, Madia Trujillo, Rafael Radi, and Dario A. Estrin. "Molecular Basis of the Mechanism of Thiol Oxidation by Hydrogen Peroxide in Aqueous Solution: Challenging the SN2 Paradigm." *Chemical Research in Toxicology* 25, no. 3 (Mar. 19, 2012): 741-46. https://doi.org/10.1021/b (200540z.

[38] De Rycker, Johan, and Barry Halliwell. Oxidation of Thiol Compounds by Catalase and Peroxidase in the Presence of Manganese (II) and Phenols. Portland Press Limited, 1978.

[39] "Innovative Plastics Oxygen and Water Permeability." http://www.pod-sabic-ip.com/KBAM/Reflection/Assets/Thumbnail/10620_4.pdf.

[40] Chaix, Estelle, Carole Guillaume, and Valerie Guillard. "Oxygen and Carbon Dioxide Solubility and Diffusivity in Solid Food Matrices: A Review of Past and Current Knowledge." *Comprehensive Reviews in Food Science and Food Safety* 13, no. 3 (May 1, 2014): 261-86. https://doi.org/10.1111/1541-4337.12058.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A product comprising a bottle containing a solution, wherein the bottle comprises at least one barrier layer, wherein an environment within the bottle not occupied by the solution is about 90% or more free of $O_2$; and
   wherein the solution comprises an effective amount of cysteamine or derivatives thereof to treat cystinosis, and an oil having a lower density than the solution.

2. The product of claim 1, wherein the barrier layer includes a layer of ethylene vinyl alcohol, aluminum foil, and an iron based absorbent layer.

3. The product of claim 1, wherein the at least one barrier layer includes three barrier layers stacked on top of one another.

4. The product of claim 1, further comprising a container, wherein the bottle is disposed within the container, wherein the environment within the container is substantially free of $O_2$.

5. The product of claim 4, wherein the container comprises at least one barrier layer, wherein each of the barrier layers reduces the amount of $O_2$ from entering the container as compared to a container without the barrier layer.

6. The product of claim 5, wherein the barrier layer includes a layer of ethylene vinyl alcohol, aluminum foil, and an iron based absorbent layer.

7. The product of claim 6, wherein the at least one barrier layer includes three barrier layers stacked on top of one another.

8. The product of claim 4, further comprising a tip having a one way valve so the solution exits the tip and air enters through a separate channel.

9. The product of claim 8, wherein the channel includes one or more chemicals to reduce the amount of $O_2$ entering the bottle.

10. The product of claim 1, further comprising a tip having a one way valve so the solution exits the tip and air enters through a separate channel.

11. The product of claim 10, wherein the channel includes one or more chemicals to reduce the amount of $O_2$ entering the bottle.

* * * * *